(12) United States Patent
Nativ et al.

(10) Patent No.: US 12,083,006 B2
(45) Date of Patent: Sep. 10, 2024

(54) SYSTEMS, DEVICES AND METHODS FOR DELIVERING SEALANTS TO TARGET TISSUE FOR CONTROLLING BLEEDING OF THE TARGET TISSUE

(71) Applicant: Ethicon, Inc., Raritan, NJ (US)

(72) Inventors: Nir I. Nativ, West Orange, NJ (US); Jared Schneider, Union, NJ (US); Geoffrey Navarro, Bridgewater, NJ (US); Brian Aitken, Bridgewater, NJ (US)

(73) Assignee: Ethicon, Inc., Raritan, NJ (US)

( * ) Notice: Subject to any disclaimer, the term of this patent is extended or adjusted under 35 U.S.C. 154(b) by 297 days.

(21) Appl. No.: 17/557,952

(22) Filed: Dec. 21, 2021

(65) Prior Publication Data
US 2023/0190439 A1 Jun. 22, 2023

(51) Int. Cl.
*A61F 2/00* (2006.01)
*A61B 17/00* (2006.01)

(52) U.S. Cl.
CPC ...... *A61F 2/0063* (2013.01); *A61B 17/00491* (2013.01); *A61B 17/0057* (2013.01); *A61F 2002/0072* (2013.01)

(58) Field of Classification Search
CPC .......... A61B 17/00491; A61B 17/0057; A61B 2017/00495; A61B 2017/00946; A61F 2/0063; A61F 2002/0072; A61L 2400/04
See application file for complete search history.

(56) References Cited

U.S. PATENT DOCUMENTS

| 3,857,395 A | 12/1974 | Johnson et al. |
| 5,395,383 A | 3/1995 | Adams et al. |
| 5,397,332 A | 3/1995 | Kammerer et al. |
| 6,589,269 B2 | 7/2003 | Zhu et al. |
| 8,372,092 B2 | 2/2013 | Gabel et al. |

(Continued)

FOREIGN PATENT DOCUMENTS

| EP | 0543499 A1 | 5/1993 |
| WO | 1999032173 A1 | 7/1999 |

OTHER PUBLICATIONS

International Search Report dated Feb. 7, 2023, from corresponding International Application No. PCT/IB2022/060795.
(Continued)

*Primary Examiner* — Mohamed G Gabr
(74) *Attorney, Agent, or Firm* — Troutman Pepper Hamilton Sanders LLP

(57) ABSTRACT

A sealant delivery device includes a housing, a matrix container connected with a distal end of the housing and being moveable between closed and opened positions, and a matrix, such as a hemostatic substrate, disposed within the matrix container. The sealant delivery device includes a sealant dispensing system in fluid communication with the matrix container that is configured for dispensing a sealant onto the matrix disposed within the matrix container. An actuator is coupled with the sealant dispensing system and the matrix container. The actuator is engageable for opening the matrix container for exposing the matrix and expressing the sealant onto the matrix. A component of the matrix container may be used to press the matrix and sealant expressed onto the matrix against target tissue to control bleeding of the target tissue.

23 Claims, 31 Drawing Sheets

(56) References Cited

U.S. PATENT DOCUMENTS

| | | |
|---|---|---|
| 9,592,108 B2 | 3/2017 | Lavigne et al. |
| 2005/0149117 A1* | 7/2005 | Khosravi ......... A61B 17/00491 |
| | | 606/215 |
| 2008/0114315 A1 | 5/2008 | Voegele et al. |
| 2012/0078293 A1 | 3/2012 | Hassidov et al. |
| 2014/0222067 A1 | 8/2014 | Ericson et al. |
| 2015/0119851 A1 | 4/2015 | Hoogenakker et al. |
| 2020/0008788 A1 | 1/2020 | Devaud et al. |

OTHER PUBLICATIONS

SURGICEL® Powder Absorbable Hemostat, www.jnjmedicaldevices.com, 2019, 8 pages, Ethicon, Inc., Somerville, New Jersey 08876.

\* cited by examiner

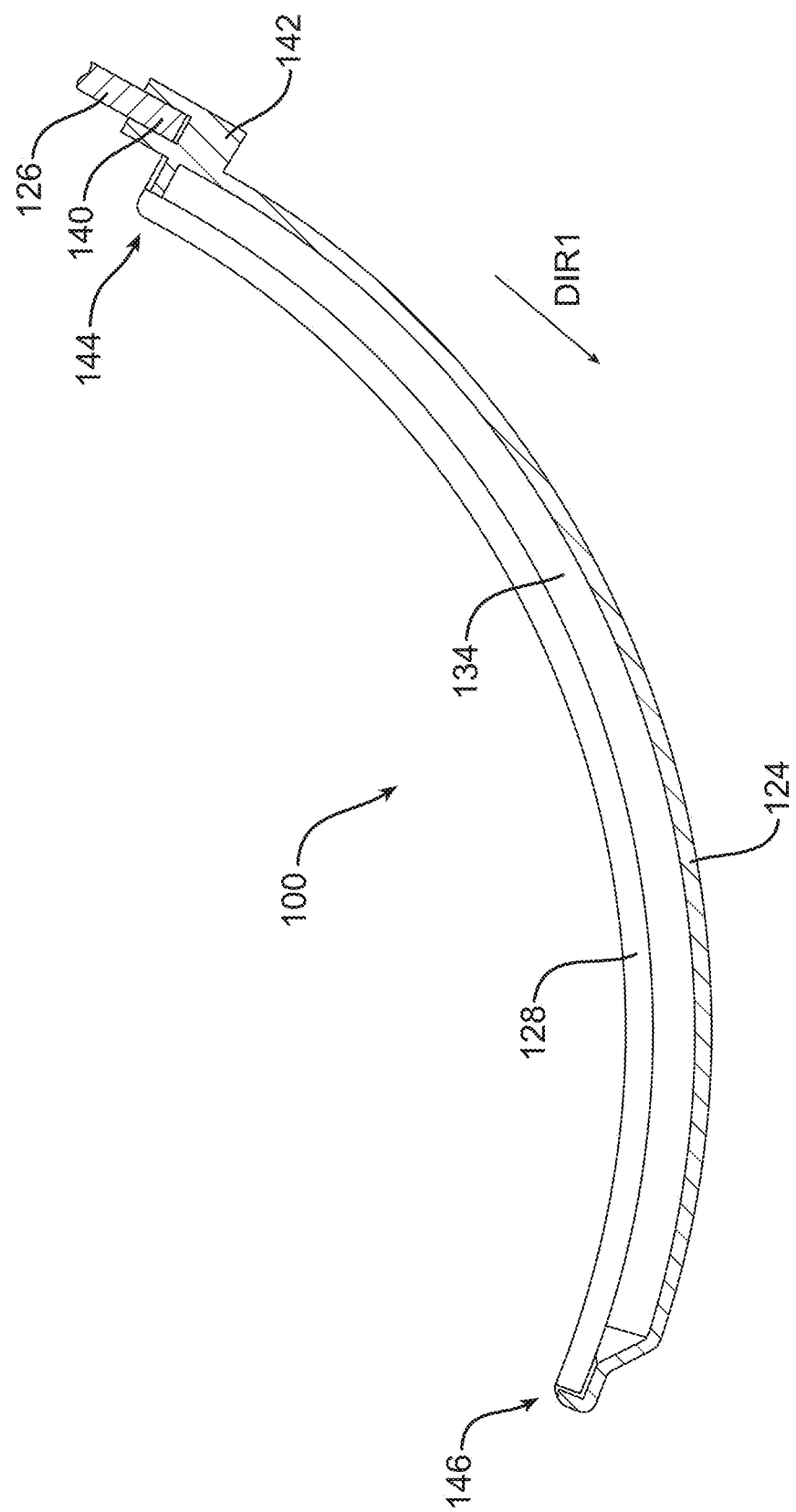

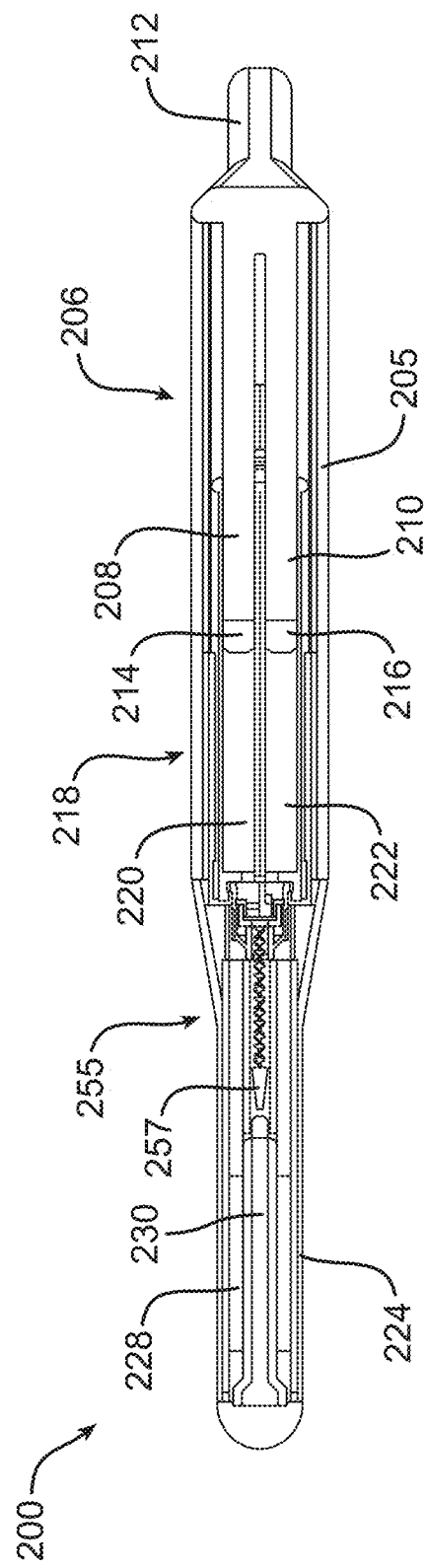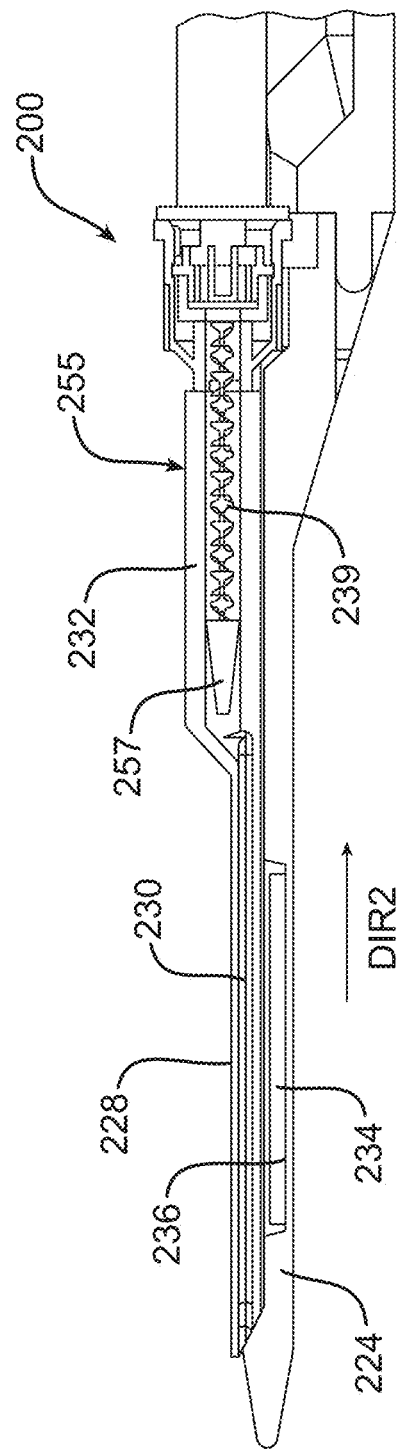
FIG. 13B
FIG. 14

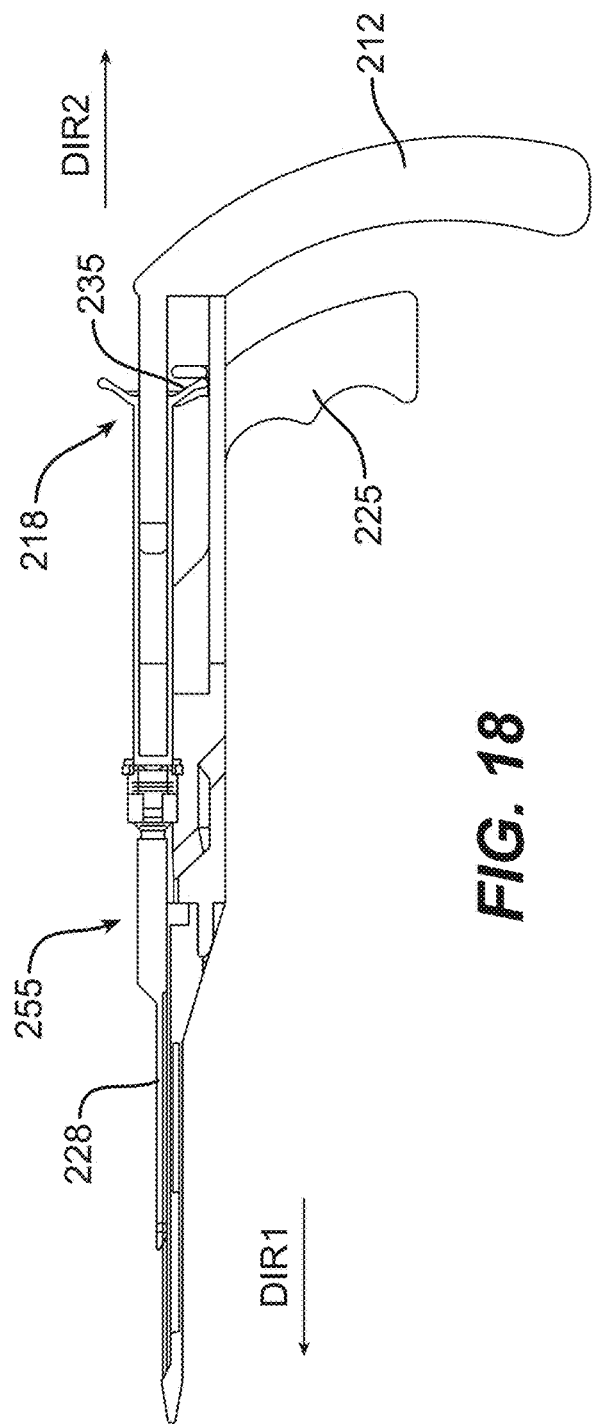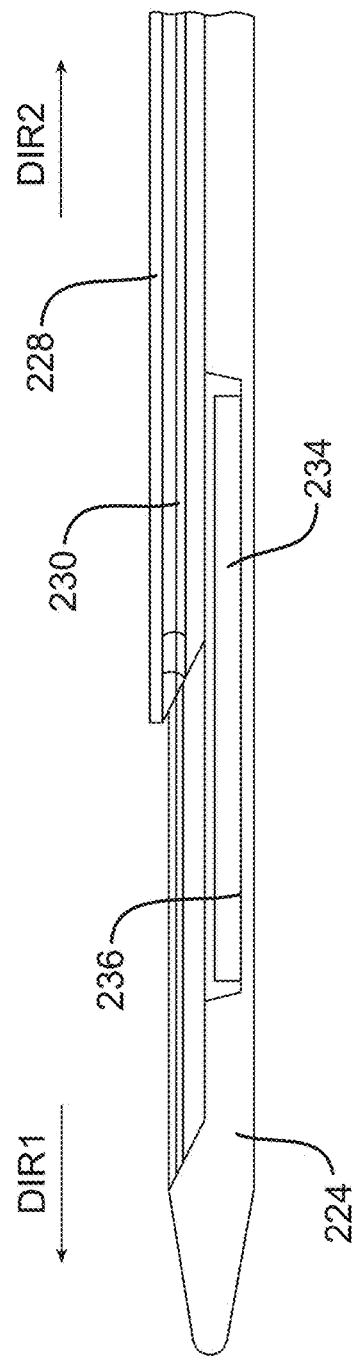

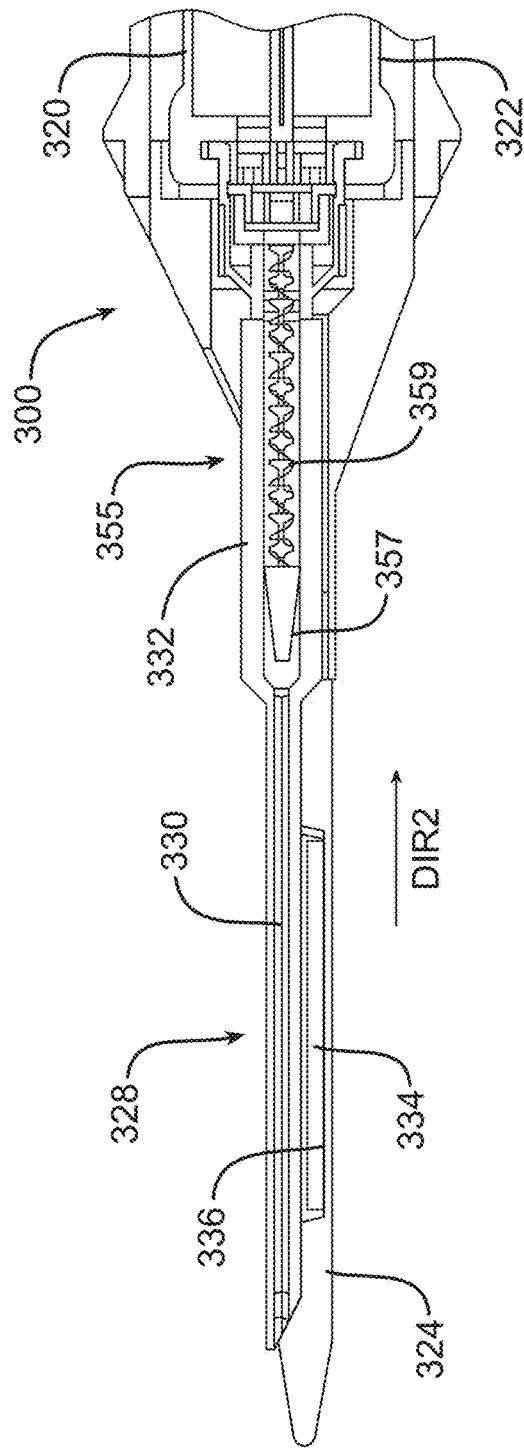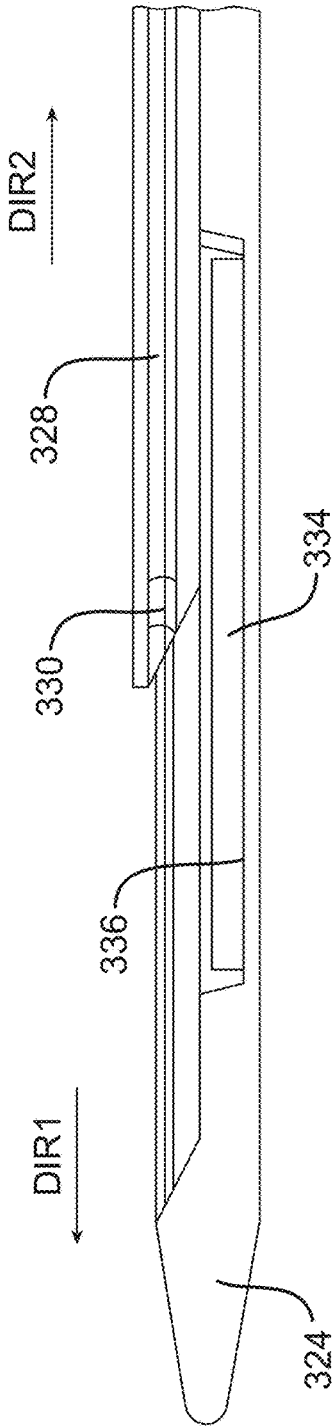
FIG. 26
FIG. 27

SYSTEMS, DEVICES AND METHODS FOR DELIVERING SEALANTS TO TARGET TISSUE FOR CONTROLLING BLEEDING OF THE TARGET TISSUE

BACKGROUND OF THE INVENTION

Field of the Invention

The present patent application is related to controlling bleeding during surgical procedures, and is more specifically related to systems, devices, and methods used for delivering sealants to target tissue for controlling bleeding of the target tissue.

Description of the Related Art

Medical textiles are used during surgical procedures to control bleeding, minimize blood loss, reduce post-surgical complications, and shorten the duration of surgery. Commonly used medical textiles include adhesion barriers, sponges, meshes, and hemostatic wound dressings that are applied to the surface of tissue. Hemostatic wound dressings include absorbable hemostats such as those sold by Ethicon, Inc. of Somerville, NJ under the registered trademarks Surgicel®, Surgicel Nu-Knit®, and Surgicel® Fibrillar.

Traditionally, medical textiles have been delivered to surgical sites using grasping instruments such as clamps and forceps. It is also well-known to use applicator instruments for delivering medical textiles. For example, U.S. Pat. No. 3,857,395 discloses an inserter device having a pair of outwardly bendable arms that bilaterally spread an adhesion barrier within a vaginal cavity.

Commonly assigned U.S. Pat. No. 5,395,383 discloses an applicator instrument used for applying a sheet of surgical material (i.e., an adhesion barrier) through an endoscopic tube. The applicator instrument includes an expandable operating tip that is insertable into an endoscopic tube to enable a surgeon to apply the surgical material to tissue inside a body. In one embodiment, the applicator instrument comprises a set of telescoping tubes including an outer delivery tube, an intermediate deployment tube, and an inner irrigation tube. The expandable operating tip is mounted at the distal end of the irrigation tube and is connected to the distal end of the deployment tube. The spreader tip is exposed at the distal end of the delivery tube by advancing the deployment tube and the irrigation tube relative to the delivery tube. The spreader tip is expanded by movement of the deployment tube relative to the irrigation tube to spread the sheet of surgical material over the tissue. A nozzle is provided at the distal end of the irrigation tube for applying a fluid, e.g., a saline solution, to the surgical material.

Commonly assigned U.S. Pat. No. 5,397,332 discloses an applicator for applying a sheet of surgical material, e.g., a surgical mesh, to internal body tissue. The applicator includes a delivery tube, a deployment tube slidably received within the delivery tube, and a shaft or irrigation tube slidably received within the deployment tube. An expandable spreader tip is connected between the distal ends of the shaft and the deployment tube. The spreader tip is collapsed and inserted in the delivery tube with the surgical mesh. The applicator is inserted through a trocar tube into a body cavity and the spreader tip is exposed by retracting the delivery tube relative to the deployment tube and shaft. The applicator has a first actuator for urging the spreader tip and surgical mesh into engagement with the tissue as the deployment tube is retracted, and a second actuator for advancing the deployment tube relative to the shaft to expand the spreader tip to apply the surgical mesh to the tissue. The spreader tip includes a plurality of flexible strips each having opposite ends pivotally connected to the distal ends of the shaft and the deployment tube. The applicator includes a return spring to bias the deployment tube proximally relative to the shaft to normally maintain the spreader tip in a collapsed configuration.

U.S. Pat. No. 6,589,269 to Zhu et al. discloses a patch and glue delivery system for closing tissue openings during surgery. In one embodiment, a patch applicator has an elongate body with an inner lumen and an outer lumen arranged concentrically. A patch is also provided. In operation, a source of vacuum draws a vacuum through the inner lumen. The inner lumen is applied to a patch to releasably hold the patch. The patch is advanced within the patient until it is placed on top of and over a wound in tissue. Flowable adhesive is injected through the outer lumen onto the patch and tissue surrounding the patch. The patch applicator holds the patch in place, allowing the adhesive to at least partially set for attaching the adhesive patch to close an opening in tissue. The applicator is then removed from the patch, thereby leaving the adhesive patch attached to tissue for closing an opening in the tissue.

U.S. Pat. No. 8,372,092 to Gabel et al., assigned to Ethicon, Inc., the disclosure of which is hereby incorporated by reference herein, teaches an instrument for controlling bleeding including an outer shaft, an intermediate shaft telescopically received within a central lumen of the outer shaft, and an inner shaft telescopically received within a central lumen of the intermediate shaft, the inner shaft having a proximal end and a distal end that extends distally from the intermediate shaft. The instrument includes a hemostat disposed at the distal end of the inner shaft, and a fluid-resistant element connected to the distal end of the outer shaft and surrounding the hemostat. The fluid-resistant element has a breakable, fluid-resistant seal at a distal end thereof that protects the hemostat from fluids until the hemostat is delivered and deployed onto tissue. In one embodiment, the instrument includes an inflatable balloon to deploy and tamponade the hemostat.

U.S. Patent Application Publication No. 20120078293 to Hassidov et al. discloses applicators for patches and adhesives. The applicators are designed for applying one or two components of a single-component or a dual-component adhesive glue or sealant to a tissue surface, thus allowing optimal on-site curing of the adhesive. During a first stage of an adhesive application procedure, a first component of the adhesive, e.g., a viscous pre-gel, is applied to the tissue surface. During a second stage of the procedure, the applicators are used to apply a patch (e.g., a solid patch) or other solid support to the tissue surface. The patch comprises a second component of the adhesive, e.g., a curing agent, such that the patch and curing agent together serve as a curing/hardening patch. The curing agent, upon contact with the pre-gel, causes the pre-gel to become more solid and to adhere to the tissue surface. The patch also provides mechanical support to the tissue surface. The applicator is typically used to hold the patch against the tissue surface for about one minute. The patch is typically left on the tissue surface, and eventually biodegrades.

U.S. Pat. No. 9,592,108 to Lavigne et al. is directed to a method of applying a surgical patch during minimally invasive surgery. The method includes laparoscopically transferring a polymeric bag containing a surgical patch into a body cavity followed by removing the surgical patch from the polymeric bag within the body cavity, and applying the surgical patch to a site in the body cavity in need of hemostasis. The hemostatic patch may include a substrate having a first hydrogel precursor applied to a first portion of the substrate, and a second hydrogel precursor applied to a second portion of the substrate.

In spite of the above advances, surgeons have continued to experience difficulties when attempting to deploy sealants (e.g., a matrix with pre-applied sealant) to certain anatomical regions of a human body, such as the posterior aspect of the thoracic aorta. When attempting to apply sealants in hard to reach locations, surgeons have found it challenging to maneuver the sealant components into place, to avoid saturating medical textiles with blood, and to complete placement before the sealant sets.

Thus, there remains a need for systems, devices and methods that protect medical textiles (e.g. a matrix; a hemostatic substrate) prior to placement of the medical textile onto target tissue.

There also remains a need for systems, devices and methods that maintain the sealant that is applied to a matrix in an unmixed state until immediately prior to placing the matrix or medical textile onto target tissue.

In addition, there is a need for systems, device and methods for delivering a matrix (e.g., a medical textile; a hemostatic substrate) to target tissue that is located in hard to reach areas of a patient's anatomy.

Moreover, there is a need for systems, devices and methods that enable a matrix to be secured over target tissue without the possibility of the matrix sticking to non-target tissue as the matrix is delivered to the target tissue.

Furthermore, there is a need for systems, devices and methods that accomplish the above while using an economy of materials.

SUMMARY OF THE INVENTION

In one embodiment, a sealant delivery device enables surgeons to control bleeding at hard to reach places of a patient's anatomy.

In one embodiment, the sealant delivery device disclosed herein enables surgeons to reliably advance a matrix (e.g., a hemostatic substrate; a medical textile) to target tissue while minimizing the likelihood of the matrix sticking to surrounding tissue as the matrix is advanced to the target tissue.

In one embodiment, a sealant delivery device preferably includes a housing, a matrix container connected with a distal end of the housing that is moveable between closed and opened positions, and a matrix (e.g., a hemostat) disposed within the matrix container.

In one embodiment, the matrix may include medical textiles, biocompatible matrices, and/or biocompatible substrates. The matrix may be used during surgical procedures for controlling and/or stopping bleeding of target tissue.

In one embodiment, the matrix may comprise any biocompatible materials capable of being coated with a sealant.

In one embodiment, the matrix may be a thin substrate, a flexible substrate and/or a flat substrate.

In one embodiment, the matrix may be absorbable or non-absorbable.

In one embodiment, the matrix may include one or more of the following: natural polymers, such as polysaccharides, such as CMC, cellulose, oxidized cellulose, oxidized regenerated cellulose, chitosan, similar materials, and combinations thereof; biological derived materials, such as proteins, gelatin, collagen, fibrin, fibrinogen, thrombin, and combinations thereof; synthetic polymers, such as polyesters, such as polylactide-co-glycolide, PTFE, TELFA, silicone, polyethylene, and non-adherent dressings known in the art; combinations of natural and synthetic polymers; woven, non-woven, knit, felt, films, textiles, and combinations thereof; porous; non-porous materials, and combinations thereof; single-layer or multi-layer substrates; substrates coated by active or reactive components or hemostatic agents; and combinations of and of the above.

In preferred embodiments, the matrix may comprise one or more of the hemostats sold by Ethicon, Inc. of Raritan, N.J. under the trademarks SURGICEL®, SURGICEL SNoW™, SURGICEL ORIGINAL®, SURGICEL NU-KNIT®, and SURGICEL FIBRILLAR®.

In one embodiment, the sealant delivery device preferably includes a sealant dispensing system in fluid communication with the matrix container. The sealant dispensing system is preferably configured for dispensing a sealant (e.g., a flowable sealant) onto the matrix that is disposed within the matrix container.

Sealants are used in a wide range of different clinical applications. Sealants can be used as both a primary and/or secondary method of joining or sealing tissue. A common class of tissue adhesives is fibrin-based and contains a concentrate of fibrinogen and thrombin. Fibrin adhesives are typically two-component adhesives that when mixed together react to simulate the last stages of the coagulation cascade. The resulting clot adheres to tissue and bridges a gap between the tissues until healing can occur. Glues based on albumin or gelatin cross-linked with an aldehyde are also known. Representative of this class of glues are gelatin-resorcinol cross-linked with formaldehyde or glutaraldehyde. Gelatin-based glues have been extensively studied and shown to generally be effective. Cyanoacrylates, polyurethanes, polymethylmethacrylates, hydrogel-forming formulations, among other synthetic polymers, have been also investigated as tissue glues. The tissue adhesives/sealants based on PEG, PEO and PoX chemistries are typically delivered as liquids that react and crosslink to form hydrogels. Various other technologies have been developed for the formulation of tissue adhesives. Some of them are of synthetic origin, such as the glues based on cyanoacrylates (2-butyl cyanoacrylate, 2-octyl cyanoacrylate), or on synthetic polymers (polyurethanes, polymethylmethacrylates) and others contain biological materials such as collagen or fibrin which, in addition, have hemostatic properties and also act by controlling bleeding. As a result of their hemostatic and adhesive properties, sealants, and particularly fibrin sealants—have been extensively used in most surgical specialties for over two decades to reduce blood loss and post-operative bleeding because of the ability to adhere to human tissue as it polymerizes.

In one embodiment, tissue sealant compositions (also referred to herein as the sealant) preferably comprise an electrophilic-containing component, such as a multi-arm polyalkylene oxide, preferably from polyethylene glycol, having at least 2 electrophilic groups and a nucleophilic containing component, such as albumin, gelatin, collagen, or a multi-arm polyalkylene oxide, preferably from polyethylene glycol, having at least 2 nucleophilic groups; and optionally a buffer. In a preferred embodiment, the sealant composition comprises a multi-arm PEG-SG (PEG-Succinimidyl Glutarate ester) and PEG-NH2 (PEG-amine) or albumin.

In one embodiment, the sealant delivery device preferably includes an actuator coupled with the sealant dispensing system and the matrix container. In one embodiment, the actuator is engageable for moving the matrix container from the closed position to the opened position for exposing the matrix while the sealant dispensing system simultaneously expresses the sealant onto the matrix.

In one embodiment, the matrix container is configured to open before the sealant is expressed onto the matrix.

In one embodiment, the sealant is expressed onto the matrix before the matrix container is opened.

In one embodiment, the sealant delivery device may include a first actuator for opening the matrix container to expose the matrix, and second actuator for expressing the sealant onto the matrix. The first and second actuators may operate independently of one another.

In one embodiment, the matrix container desirably includes a tray having a proximal end connected with the distal end of the housing and a distal end that defines a distal-most end of the sealant delivery device. The tray may be malleable and may be transformed into various shapes (e.g., a curved shape). The tray may incorporate one or more wires for holding the transformed shape of the tray.

In one embodiment, the matrix container desirably includes a protective cover that overlies the tray and that is coupled with the actuator. In one embodiment, the protective cover is moveable between an extended position that defines the closed position of the matrix container and a retracted position that defines the opened position of the matrix container.

In one embodiment, the protective cover is configured to move simultaneously with the actuator as the actuator is pulled toward the proximal end of the housing.

In one embodiment, the tray may include a trough that is configured to receive the matrix that is disposed within the matrix container.

In one embodiment, the protective cover preferably includes a sealant dispensing channel that extends along the length of the protective cover and that is in fluid communication with the sealant dispensing system. In one embodiment, the protective cover desirably includes a sealant dispensing opening located at a distal end of the sealant dispensing channel that is configured for expressing the sealant onto the matrix as the protective cover moves from the closed position to the opened position.

In one embodiment, the actuator may include a handle secured to a proximal end of the housing, and a trigger coupled the housing and projecting from an underside of the housing. In one embodiment, the trigger is squeezable toward the handle and the proximal end of the housing for activating the sealant dispensing system while simultaneously retracting the protective cover toward the proximal end of the housing for moving the protective cover into the open position.

In one embodiment, the sealant dispensing system may include a dual barrel syringe disposed within the housing including a first syringe barrel containing a first part of the sealant and a second syringe barrel containing a second part of the sealant.

In one embodiment, the first and second parts of the sealant are mixed together to provide the sealant that is expressed onto the matrix for controlling bleeding of tissue. The first and second parts of the sealant may chemically react with one another to form the sealant that may be used for controlling bleeding. The sealant is preferably biocompatible and may be absorbed over time into a patient's body.

In one embodiment, a first syringe plunger is disposed within the first syringe barrel and has a proximal end connected with the proximal end of the housing.

In one embodiment, a second syringe plunger is disposed within the second syringe barrel and has a proximal end connected with the proximal end of the housing.

In one embodiment, the trigger is preferably coupled with the dual barrel syringe for pulling the dual barrel syringe toward the proximal end of the housing when the trigger is squeezed toward the handle and the proximal end of the housing.

In one embodiment, when the trigger is squeezed toward the proximal end of the housing, the first syringe plunger forces the first part of the sealant from the distal end of the first syringe barrel and the second syringe plunger forces the second part of the sealant from the distal end of the second syringe barrel.

In one embodiment, the sealant delivery device preferably includes a sealant mixer disposed between the first and second syringe barrels and the fluid dispensing channel of the protective cover for mixing the first and second parts of the sealant together and delivering the mixed sealant into the sealant dispensing channel of the protective cover.

In one embodiment, the sealant mixer may include a sealant mixing tube having a proximal and a distal end, a static mixer disposed within the sealant mixing tube, and a syringe barrel connector coupled with the proximal end of the sealant mixing tube for forming a fluid connection between distal ends of the respective first and second syringe barrels and the sealant mixing tube.

In one embodiment, the dual barrel syringe, the sealant mixer and the protective cover are configured to move together toward the proximal end of the housing as the trigger is squeezed toward the proximal end of the housing.

In one embodiment, a sealant delivery device preferably includes a housing having a proximal end and a distal end, a matrix container connected with the distal end of the housing, and a matrix (e.g., a hemostatic substrate; a medical textile) disposed within the matrix container In one embodiment, the matrix container preferably includes a protective cover that is movable between an extended position (e.g., a closed position) and a retracted position (e.g., an opened position). In one embodiment, the protective cover has a sealant dispensing channel extending along the length thereof.

In one embodiment, the sealant delivery device preferably includes a sealant dispensing system in fluid communication with the sealant dispensing channel of the protective cover.

In one embodiment, the sealant delivery device may include an actuator coupled with the sealant dispensing system and the protective cover of the matrix container. In one embodiment, the actuator is engageable for moving the protective cover into the retracted position for opening the matrix container and activating the sealant dispensing system for expressing the sealant through the sealant dispensing channel of the protective cover and onto the matrix disposed within the matrix container.

In one embodiment, the actuator is engageable for moving the protective cover into the retracted position for opening the matrix container to expose the matrix while the sealant dispensing system simultaneously expresses the sealant through the sealant dispensing channel of the protective cover and onto the matrix disposed within the matrix container.

In one embodiment, the protective cover may include the sealant dispensing channel extending along the length of the protective cover, the sealant dispensing channel being in fluid communication with the sealant dispensing system, and a sealant dispensing opening located at a distal end of the sealant dispensing channel that is configured for expressing the sealant onto the matrix as the protective cover moves into the retracted position for opening the matrix container.

In one embodiment, the actuator may include a handle secured to the proximal end of the housing, and a trigger coupled with the housing and being slidable between the proximal and distal ends of the housing.

In one embodiment, the trigger is squeezable toward the handle and the proximal end of the housing for activating the sealant dispensing system while simultaneously moving the protective cover into the retracted position for opening the matrix container.

In one embodiment, the sealant dispensing system of the sealant delivery device may include a dual barrel syringe disposed within the housing including a first syringe barrel containing a first part of the sealant and a second syringe barrel containing a second part of the sealant.

In one embodiment, the sealant dispensing system desirably includes a first syringe plunger disposed within the first syringe barrel and having a proximal end connected with the proximal end of the housing, and a second syringe plunger disposed within the second syringe barrel and having a proximal end connected with the proximal end of the housing.

In one embodiment, the trigger is coupled with the dual barrel syringe for pulling the dual barrel syringe toward the proximal end of the housing when the trigger is squeezed toward the handle and the proximal end of the housing.

In one embodiment, when the trigger is squeezed toward the proximal end of the housing, the first syringe plunger forces the first part of the sealant from the distal end of the first syringe barrel and the second syringe plunger forces the second part of the sealant from the distal end of the second syringe barrel.

In one embodiment, the dual barrel syringe and the protective cover preferably move together toward the proximal end of the housing as the trigger is squeezed toward the proximal end of the housing.

In one embodiment, the sealant delivery device preferably includes a sealant mixer disposed between the first and second syringe barrels and the fluid dispensing channel of the protective cover for mixing the first and second parts of the sealant together and delivering the mixed sealant into the sealant dispensing channel of the protective cover.

In one embodiment, the sealant mixer may include a sealant mixing tube having a proximal and a distal end, a static mixer disposed within the sealant mixing tube, and a syringe barrel connector coupled with the proximal end of the sealant mixing tube for providing fluid communication between distal ends of the respective first and second syringe barrels and the sealant mixing tube.

In one embodiment, a method of controlling bleeding desirably includes obtaining a sealant delivery device including a housing, a matrix container connected with a distal end of the housing, a matrix disposed within the matrix container, a sealant delivery system in fluid communication with the matrix container, and an actuator for opening the matrix container to expose the matrix and express the sealant onto the matrix.

In one embodiment, the method preferably includes opening the matrix container while simultaneously expressing the sealant from the sealant delivery system onto the matrix.

In one embodiment, the method of controlling bleeding may include pulling the actuator toward a proximal end of the housing for opening the matrix container to expose the matrix while expressing the sealant onto the matrix.

In one embodiment, the method of controlling bleeding may include using a component of the matrix container (e.g., a malleable tip; the tray) to press the matrix and the sealant expressed onto the matrix against target tissue for controlling bleeding of the target tissue.

In one embodiment, a sealant delivery device preferably includes a dual barrel syringe that contains a two-part sealant that is directed through a sealant mixer and a sealant delivery channel of a protective cover. In one embodiment, the sealant delivery channel preferably widens and/or opens on an underside of the protective cover, at or adjacent the distal end of the protective cover.

In one embodiment, the sealant delivery device preferably includes a matrix container that holds a matrix (e.g., a medical textile; a hemostatic substrate). In one embodiment, the matrix container preferably includes a tray and the protective cover that overlies the tray and the matrix disposed within the tray. The tray may be flexible (e.g., malleable) and may include one or more embedded malleable wires that enable the tray to be shaped into a desired semi-rigid, curved configuration.

In one embodiment, the sealant delivery device preferably includes a push rod that interconnects the proximal end of the tray to a syringe plunger.

In one embodiment, the tray, the matrix, and the protective cover may be bent into a desired shape and maneuvered into position inside a patient. In one embodiment, as the dual barrel syringe is actuated (e.g., the plunger is held stationary while the syringe body is translated proximally), the protective cover translates proximally to progressively expose and/or uncover the matrix, while the sealant is mixed and expressed over the surface of the matrix. The sealant delivery device may be used to press the matrix and the expressed sealant against target tissue for controlling bleeding of the target tissue.

In one embodiment, the tray is preferably covered by the protective cover (e.g.; a slidable protective cover) that prevents the matrix from contacting outside moisture prior to deployment of the matrix onto the target tissue. Protecting and isolating the matrix prior to placement on target tissue provides many benefits including minimizing fluid runoff during access/positioning; minimizing fluid contact with unintended anatomy; and mixing the reactive components of the sealant only after the matrix is already in position at the target tissue, thus reducing any concerns around insufficient working time.

In one embodiment, the sealant delivery device preferably stores a flat matrix (e.g., a medical textile; a biocompatible patch; a biocompatible matrix) in a tray that is covered by the slidable, protective cover. In one embodiment, during deployment of the matrix onto target tissue (e.g., a wound), the protective cover may be retracted for exposing the matrix while the device expresses (e.g., simultaneously expresses) a sealant fluid that comprises a mixture of reactive components from the dual barrel syringe onto the exposed matrix. The matrix, infused with the sealant, may be pressed against the target tissue with the sealant fluid facing the target tissue.

In one embodiment, the distal end of the tray may have a "duckbill tip" for ease of insertion into a patient. The tray may be used as a tamponade to hold the matrix against the tissue while the sealant (e.g., a tissue adhesive) cures.

In one embodiment, a sealant delivery device preferably has a trigger design that enables the matrix (e.g., a medical textile; a hemostatic substrate) to remain stationary relative to target tissue as the protective cover is retracted and sealant is delivered to the matrix. In one embodiment, the sealant delivery device includes a housing that is connected directly to the tray (e.g., a malleable tray). The dual barrel syringe is connected directly to the trigger. The trigger may be squeezed toward the proximal end of the housing to pull the dual barrel syringe toward the proximal end of the housing, which forces the two parts of the sealant of the two syringe barrels to flow into the sealant dispensing channel of the protective cover.

In one embodiment, during an initial stage of delivering a sealant to target tissue, the matrix is protected by the protective cover and the two parts of a sealant are not yet mixed together.

In one embodiment, the tray (e.g., a malleable tip) may be pre-bent to a desired shape (e.g., a shape for accessing the posterior side of anastomosis; a curved shape).

In one embodiment, depressing one or more plungers forces the two parts of the sealant to flow through a static mixer and through a sealant dispensing channel formed in the protective cover. Upon reaching a sealant dispensing opening at the distal end of the protective cover, the mixed sealant spreads over the matrix disposed within the tray as the protective cover slides relative to the tray for exposing the matrix.

In one embodiment, engaging an actuator (e.g., a trigger; a thumb tab) retracts a dual barrel syringe to force the two parts of a sealant to flow through a static mixer and a sealant dispensing channel formed in the protective cover. The mixed sealant spreads over the matrix as the protective cover moves (e.g., slides) relative to the tray for exposing the matrix (e.g., a medical textile; a hemostatic substrate).

In one embodiment, the sealant flows distally through the protective cover as the protective cover moves relative to the tray to expose the matrix.

In one embodiment, a sealant delivery device may include a push rod that interconnects a plunger and the tray.

In one embodiment, the push rod extends along the length of the device and between the two barrels of a dual barrel syringe In one embodiment, a sealant delivery device is preferably configured for delivering a two part sealant onto a matrix (e.g., a hemostat) for controlling bleeding of target tissue during open surgery. The sealant delivery device enables surgeons to effectively deliver a matrix/liquid sealant combination to target tissue of a patient. The device includes a protective cover that protects the matrix from contacting a wet field until the matrix is effectively positioned at the target tissue. Once the matrix is positioned where intended (e.g., at the target tissue), a single motion (e.g., pulling a trigger; engaging an actuator) will expose the matrix to the target tissue while delivering the mixed sealant onto the matrix. The matrix/liquid sealant combination may then be pressed against the target tissue for controlling bleeding of the target tissue.

In one embodiment, the protective cover has a sealant delivery channel that is in fluid communication with the two part sealant disposed within the dual barrel syringe. In one embodiment, the trigger design enables the dual barrel syringe to be pulled back toward the proximal end of the device, instead of pushed forward toward the distal end of the delivery device, which allows the tray that holds the matrix to remain stationary, providing an effective way to guarantee accurate matrix/sealant placement onto the target tissue for controlling bleeding.

In one embodiment, the sealant delivery device preferably includes a mixing element (e.g., a static mixer) that ensures effective mixing of the two part sealant. After the matrix has been infused with the sealant, the matrix/sealant combination may be pressed onto the bleeding source by the tray (e.g., a malleable tip) until the bleeding is controlled and/or stopped. Once bleeding is resolved, the sealant delivery device may be extracted from the patient, while leaving the matrix/sealant combination behind for controlling bleeding of the target tissue.

In one embodiment, squeezing the trigger results in the simultaneous retraction of the cover and the syringes of the dual barrel syringe, which simultaneously uncovering the matrix and expressing the mixed sealant over the exposed matrix.

In one embodiment, the sealant spreads distally as the cover is retracted to expose the matrix.

In one embodiment, a sealant delivery device may include a sealant mixer that is configured for mixing the reactive components to form a flowable, curable sealant (e.g., a tissue adhesive) that is applied to the matrix.

In one embodiment, the tray is covered by the protective cover for preventing contact of the matrix with outside moisture prior to deployment and tamponade of the matrix.

In one embodiment, the protective cover is configured to move relative to the tray (e.g., be retracted) for exposing the matrix that is disposed within the tray.

In one embodiment, the sealant dispensing channel of the protective cover is configured for directing a flowable sealant onto the matrix during retraction of the protective cover.

In one embodiment, actuating the dual barrel syringe for expressing the reactive components of the sealant simultaneously retracts the protective cover for exposing the matrix.

In one embodiment, partial retraction of the protective cover expresses a portion of the sealant onto the matrix.

In one embodiment, full retraction of the protective cover preferably expresses all of the sealant fluid that is disposed in the dual barrel syringe.

In one embodiment, a push or pull rod may be connected with the dual barrel syringe actuating mechanism.

In one embodiment, the syringe actuating mechanism is configured to retract the protective lid from the tray while simultaneously expressing the sealant (e.g., adhesive fluid) onto the matrix.

In one embodiment, retraction of the protective cover relative to the tray may be performed by pulling the protective cover toward the dual barrel syringe or pushing the tray away from the dual barrel syringe.

In one embodiment, the dual barrel syringe is mounted within a housing of a hand-operated handle/pistol grip assembly, whereby squeezing a trigger simultaneously activates expression of the reactive components from the dual barrel syringe and retracts the protective cover (e.g., a lid) for exposing the matrix.

In one embodiment, the dual barrel syringe may be mounted within a robot-operated mount having actuators that are configured to simultaneously activate expression of the reactive components from the dual barrel syringe and retract the protective cover to expose the matrix.

In one embodiment, a sealant delivery device may be configured so that expressing and mixing the reactive components of the sealant is initiated prior to initiating the retraction of the protective cover, whereby the delay in the retraction of the protective cover provides additional time for filling of the sealant dispensing channel of the protective cover with the curable sealant fluid.

In one embodiment, a sealant delivery device may include a hand-operated handle/pistol grip assembly with a three-way valve for connecting to an external compartment or external syringe for pre-mixing/reconstituting reactive components in the dual barrel syringe prior to co-expressing and mixing the reactive components.

In one embodiment, a sealant delivery device may include a three-way luer, which allows additional syringes to be connected to the device for reconstituting the content of the dual barrel syringe.

In one embodiment, the tray may include a backing component, which is adjustable to accommodate unwanted sliding of the cover while the sealant flows to the tip of the tray.

These and other preferred embodiments of the present patent application will be described in more detail below.

BRIEF DESCRIPTION OF THE DRAWINGS

FIG. 4 is a cross-sectional view of a distal end of a sealant delivery device including a tray, a matrix disposed within the tray, a protective cover overlying the matrix, and a push rod connected with a proximal end of the tray, in accordance with one embodiment of the present patent application.

FIG. 13B is another cross-sectional view of the sealant delivery device shown in FIGS. 9A-9B and 10.

FIG. 14 is a cross-sectional view of a distal end of the sealant delivery device shown in FIGS. 9A-9B and 10 including the mixing tip, the tray, the matrix disposed within the tray, and the protective cover overlying the matrix and the tray.

FIG. 18 shows the sealant delivery device of FIGS. 9A-9B, 10, and 15 after the trigger has been squeezed toward the handle for retracting the protective cover to at least partially expose the matrix disposed within the tray.

FIG. 19 is a magnified view of the distal end of the sealant delivery device shown in FIG. 18 including the tray, the matrix, and the protective cover in a retracted position for at least partially exposing the matrix.

FIG. 26 is a magnified, cross-sectional view of the distal end of the sealant delivery device shown in FIG. 25.

FIG. 27 shows the distal end of the sealant delivery device shown in FIG. 26 after the protective cover has been partially retracted for partially exposing the matrix that is disposed within the tray.

DETAILED DESCRIPTION OF PREFERRED EMBODIMENTS

Figure 1:
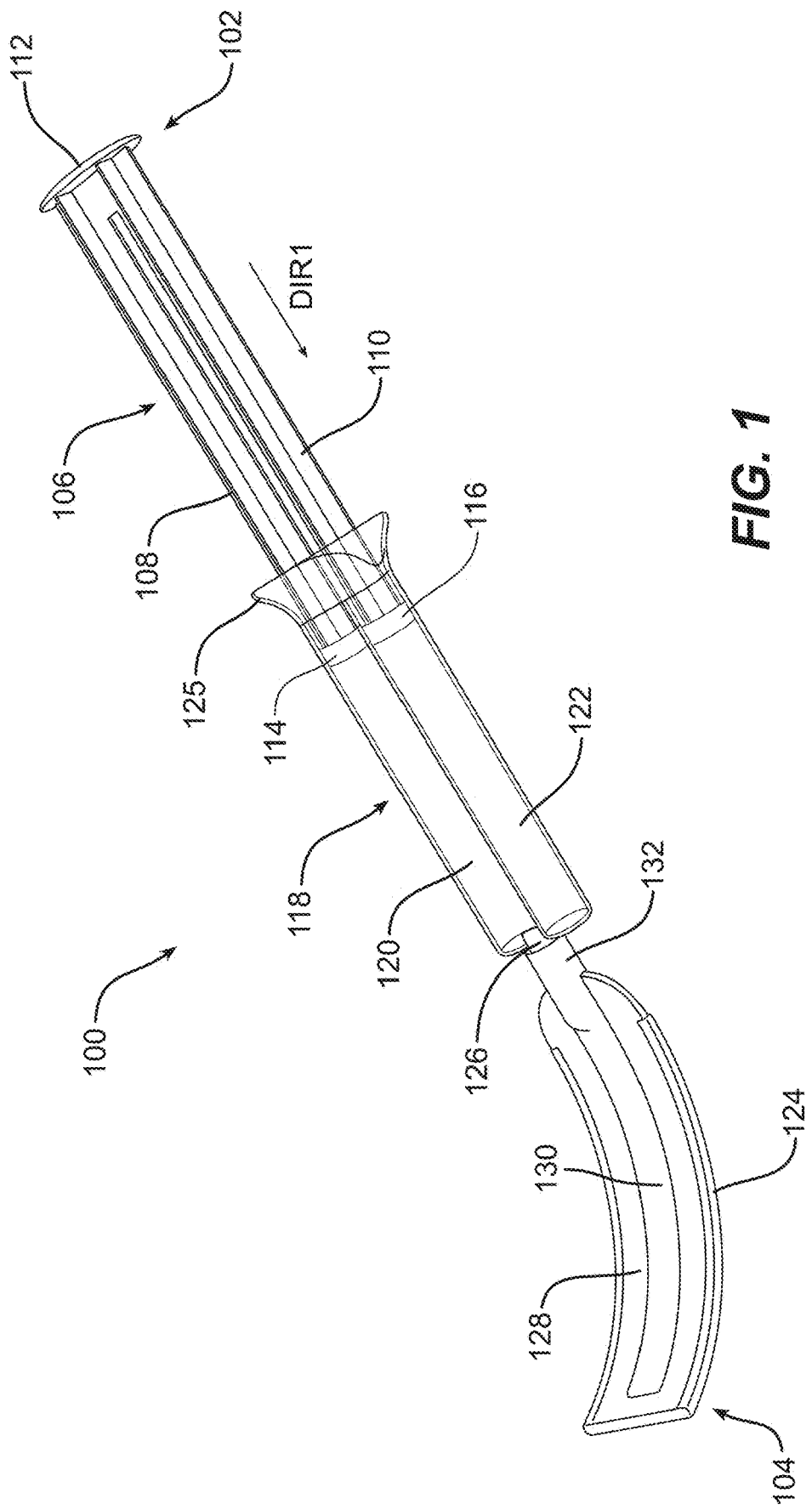
FIG. 1 is a perspective view of a sealant delivery device, in accordance with one embodiment of the present patent application.
Figure 2:
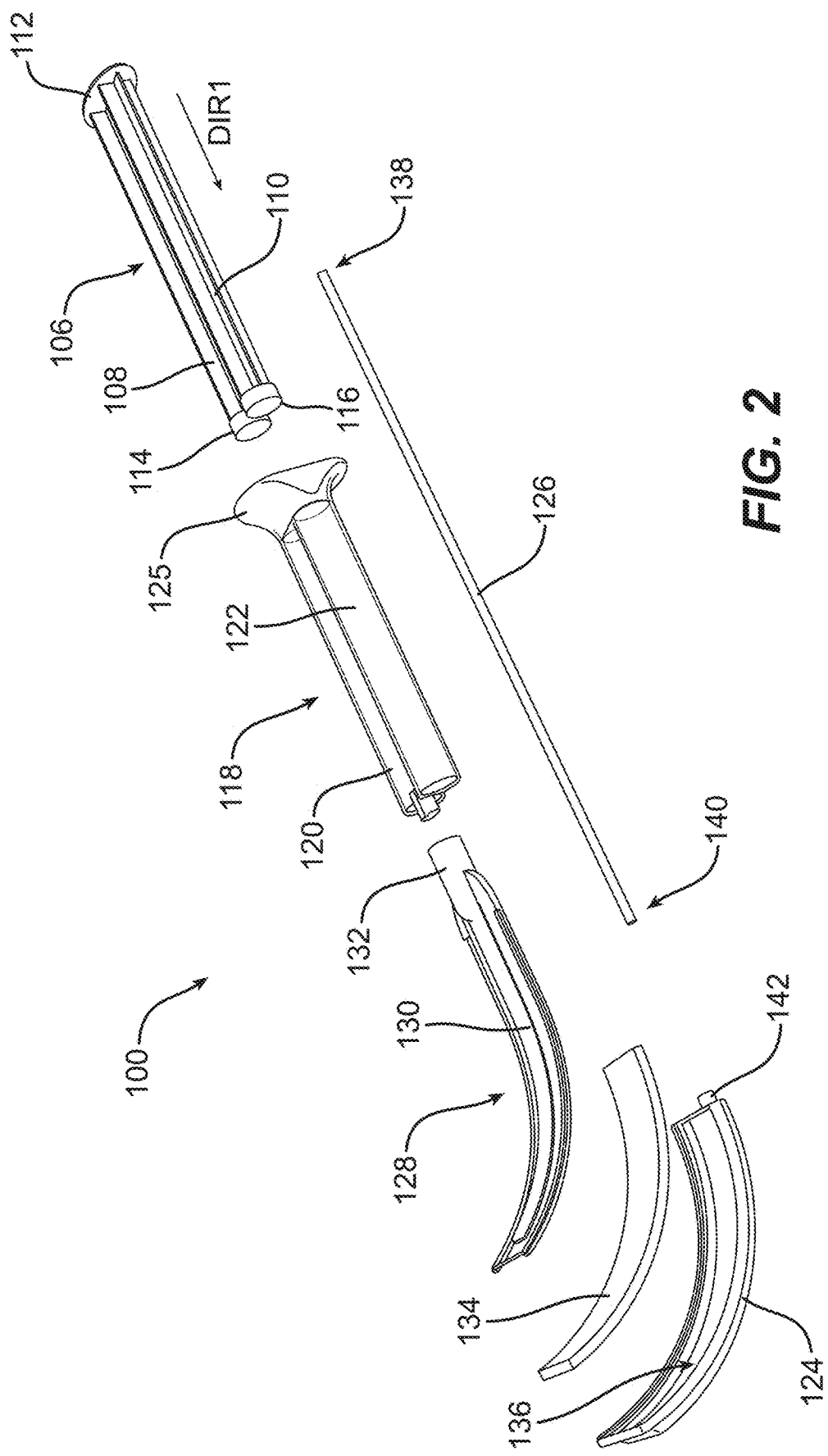
FIG. 2 is an exploded of the sealant delivery device shown in FIG. 1 including a double plunger, a dual barrel syringe, a push rod, a protective cover, a matrix, and a tray, in accordance with one embodiment of the present patent application.

Referring to FIGS. 1 and 2, in one embodiment, a sealant delivery device 100 is configured for enabling medical personnel to protect a matrix (e.g., a hemostatic matrix; a hemostatic substrate) as it is delivered to target tissue, and then, after the matrix has been positioned near the target tissue, express a sealant onto the matrix as the matrix is simultaneously exposed to the target tissue for placement onto the target tissue.

In preferred embodiments, the matrix may comprise one or more of the hemostats sold by Ethicon, Inc. of Raritan, N.J. under the trademarks SURGICEL®, SURGICEL SNoW™, SURGICEL ORIGINAL®, SURGICEL NU-KNIT®, and SURGICEL FIBRILLAR®.

In one embodiment, the sealant delivery device 100 preferably has a proximal end 102 that is normally positioned closer to an operator (e.g., a surgeon) and a distal end 104 that is normally positioned further away from the operator. In one embodiment, the sealant delivery device 100 preferably includes a double plunger 106 including a first plunger 108, and a second plunger 110 that are joined together at the respective proximal ends thereof by a depressible thumb tab 112. The sealant delivery device 100 preferably includes a first piston 114 hat is secured to a distal end of the first plunger 108 and a second piston 116 that is secured to a distal end of the second plunger 110.

In one embodiment, the sealant delivery device 100 preferably includes a dual barrel syringe 118 having a first syringe barrel 120 and a second syringe barrel 122. In one embodiment, a first part of a flowable, curable sealant may be disposed within the first syringe barrel 120 and a second part of the flowable, curable sealant may be disposed within the second syringe barrel 122. In one embodiment, the two parts of the flowable sealant may be mixed together for forming a sealant that is expressed onto a matrix (e.g., a hemostatic matrix; a hemostatic patch), as will be described in more detail herein. The matrix, infused with the sealant, may be placed onto the target tissue for controlling bleeding.

In one embodiment, the curable, flowable sealant may comprise an electrophilic-containing component, such as a multi-arm polyalkylene oxide, preferably from polyethylene glycol, having at least 2 electrophilic groups and a nucleophilic containing component, such as albumin, gelatin, collagen, or a multi-arm polyalkylene oxide, preferably from polyethylene glycol, having at least 2 nucleophilic groups; and optionally a buffer. In a preferred embodiment, the sealant may comprise a multi-arm PEG-SG (PEG-Succinimidyl Glutarate ester) and PEG-NH2 (PEG-amine) or albumin.

In one embodiment, the dual barrel syringe 118 preferably has gripping structure 125 located at a proximal end thereof. In one embodiment, the gripping structure 125 may be gripped by a surgeon's fingers as the thumb tab 112 of the double plunger 106 is engaged by the surgeon's thumb. In one embodiment, the gripping structure 125 is utilized for pulling the dual barrel syringe 118 in the proximal direction DIR2 as the thumb tab 112 is depressed in the opposite, distal direction DIR1, whereupon the first and second plungers 108, 110 force the first and second parts of the flowable sealant from the distal ends of the respective first and second syringe barrels 120, 122 for being mixed together within a syringe barrel connector 132.

In one embodiment, the sealant delivery device 100 preferably includes a matrix container (e.g., a protective structure) that protects the matrix from surrounding tissue and/or moisture as the matrix is advanced into a patient and until the matrix is delivered to the target tissue, whereupon the matrix container may be manipulated and/or moved (e.g., retracted; extended; opened) for exposing the matrix to the surrounding environment and/or target tissue for being applied to the target tissue. In one embodiment, the matrix container may include a tray 124 that is located at the distal end 104 of the sealant delivery device. In one embodiment, the tray 124 may be coupled with the thumb tab 112 of the double plunger 106 via a push rod 126, whereby depressing the thumb tab 112 in the distal direction DIR1 also moves the tray 124 in the distal direction DIR1.

In one embodiment, the matrix container of the sealant delivery device 100 preferably includes a protective cover 128 that overlies a top side of the tray 124. In one embodiment, the protective cover 128 preferably includes a sealant dispensing channel 130 that extends along the length of the protective cover 128 and the syringe barrel connector 132 that is utilized for forming a fluid connection with dispensing openings located at the distal ends of the respective first and second syringe barrels 120, 122.

Although not shown in FIG. 1, in one embodiment, the sealant delivery device 100 may include a static mixer that is disposed within a lumen of the syringe barrel connector 132 for mixing the first and second parts of the sealant that are dispensed from the distal ends of the respective first and second syringe barrels 120, 122. In one embodiment, the sealant preferably flows distally through the lumen of the syringe barrel connector 132 and into the sealant dispensing channel 130 for being expressed onto the matrix. In one embodiment, the sealant may be dispensed from the protective cover 128 as the tray 124 is being extended for exposing the matrix 134.

In one embodiment, the tray 124 has a trough 136 (e.g., a pocket; a depression) and the matrix 134 is disposed within the trough 136 of the tray 124.

In one embodiment, the push rod 126 preferably has a proximal end 138 that is connected with the thumb tab 112 of the double plunger 106 and a distal end 140 that is inserted into a push rod connector 142 located at a proximal end of the tray 124. In one embodiment, as the thumb tab is depressed in the distal direction DIR1, the push rod moves distally for extending the tray 124 relative to the protective cover 128. As the tray 124 is extended relative to the protective cover 128, the matrix disposed within the trough 136 of the tray 124 is exposed.

Figure 3A:
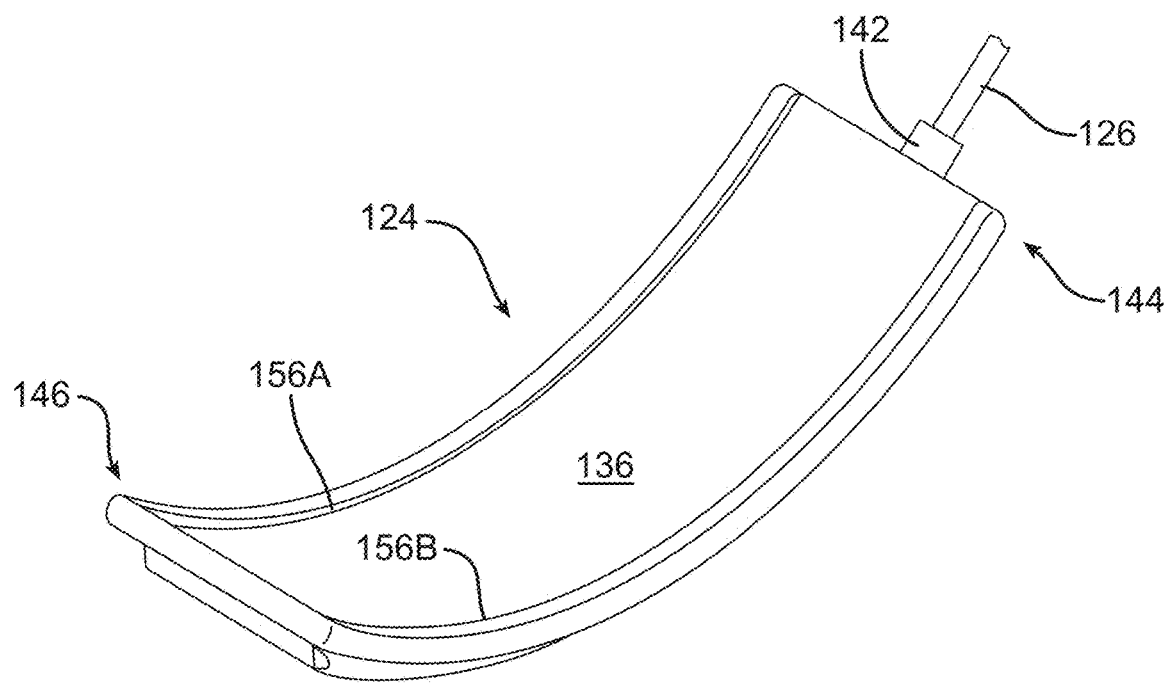
FIG. 3A is a perspective view of a top side of the tray shown in FIG. 2.
Figure 3B:
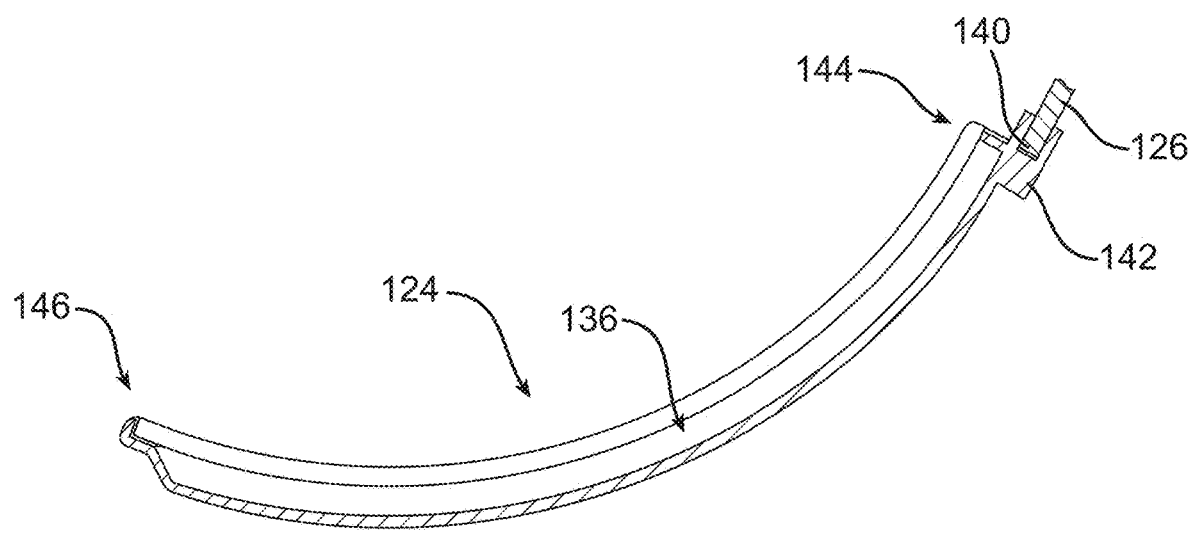
FIG. 3B is a cross-sectional view of the tray shown in FIG. 3A.

Referring to FIGS. 3A and 3B, in one embodiment, the tray 124 of the sealant delivery device 100 (FIG. 1) preferably includes a proximal end 144 and a distal end 146. The tray 124 preferably includes the trough 136 that extends between the proximal and distal ends 144, 146, which is adapted to receive the matrix 134 (FIG. 2).

In one embodiment, the tray 124 preferably includes the push rod connector 142 located at the proximal end 144 of the tray 124, which is adapted to receive the distal end 140 of the push rod 126 (FIG. 2). The proximal end of the push rod 126 is connected with the thumb tab 112 (FIG. 1) of the double plunger 106. In one embodiment, depressing the thumb tab slides the double plunger and the push rod toward the distal end of the sealant delivery device, which, in turn, extends the tray 124 from the distal end of the sealant delivery device.

Referring to FIG. 4, in one embodiment, the matrix 134 is preferably disposed within the trough 136 (FIG. 3B) of the tray 124. The matrix 134 preferably extends along the length of the tray 124 and is located between the proximal end 144 and the distal end 146 of the tray. In one embodiment, the distal end 140 of the push rod 126 is secured to the push rod connector 142 located at the proximal end 144 of the tray 124, In one embodiment, the sealant delivery device 100 preferably includes the protective cover 128 that overlies the matrix 134 and the tray 124, As will be described in more detail herein, in one embodiment, the push rod 126 may be utilized for moving the tray 124 and the matrix 134 in the distal direction designated DIR1 relative to the protective cover 128, which remains stationary, for exposing the matrix 134 at the distal end of the sealant delivery device.

Figure 5A:
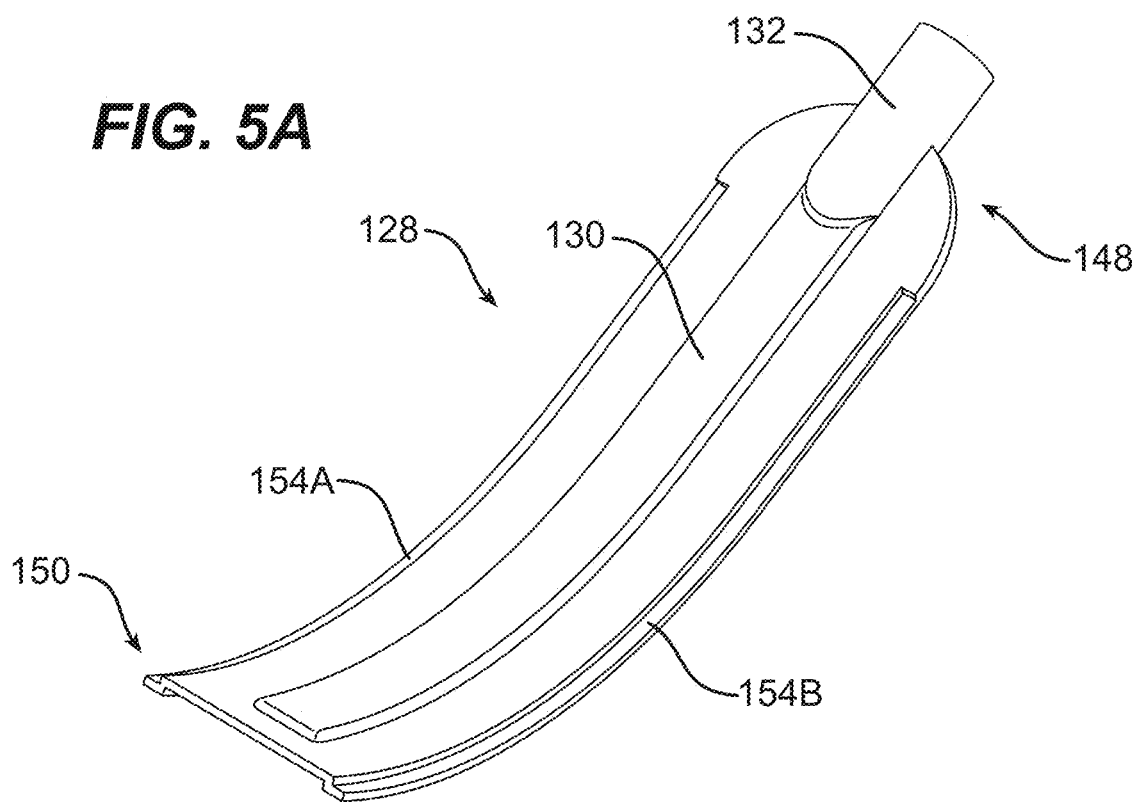
FIG. 5A is a perspective view of a top side of the protective cover shown in FIG. 2.
Figure 5B:
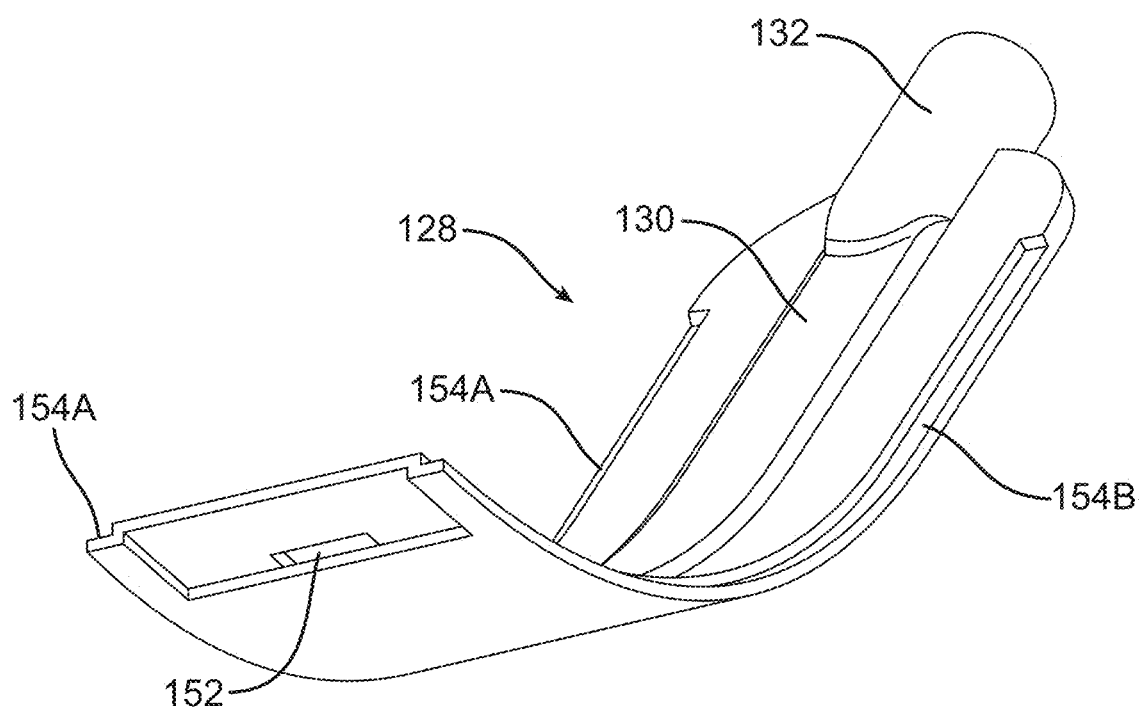
FIG. 5B is a perspective view of an underside of the protective cover shown in FIG. 5A.

Referring to FIGS. 5A and 5B, in one embodiment, the protective cover 128 of the sealant delivery device 100 (FIG. 1) preferably has a proximal end 148 and a distal end 150. The protective cover 128 preferably includes the syringe barrel connector 132 that is preferably adapted for being in fluid communication with the distal ends of the respective first and second syringe barrels 120, 122 (FIGS. 1 and 2) for directing the first and second parts of the flowable, curable sealant into the channel 130 of the protective cover 128. In one embodiment, the channel 130 is preferably adapted for dispensing the flowable sealant from a sealant dispensing opening 152 located at the distal end 150 of the protective cover 128. In one embodiment, the channel 130 preferably extends from the syringe barrel connector 132 to the sealant dispensing opening 152 at the distal end of the channel 130.

In one embodiment, a static mixer (not shown) may be disposed within the lumen of the syringe barrel connector 132. The static mixer is preferably configured for mixing the first and second parts of the flowable, curable sealant together as the flowable sealant moves distally through the syringe barrel connector 132. The static mixer may be similar to that shown in FIGS. 11A and 11B of the present patent application.

In one embodiment, the protective cover 128 preferably includes first and second lateral guide slots 154A, 154B that preferably extend along the length of the protective cover 128 between the proximal end 148 and the distal end 150 thereof. The first and second lateral guide slots 154A, 154B preferably mesh with respective lateral guide flanges 156A, 158B provided on the tray 124 for guiding sliding movement of the tray 124 relative to the protective cover 128.

Figure 6A:
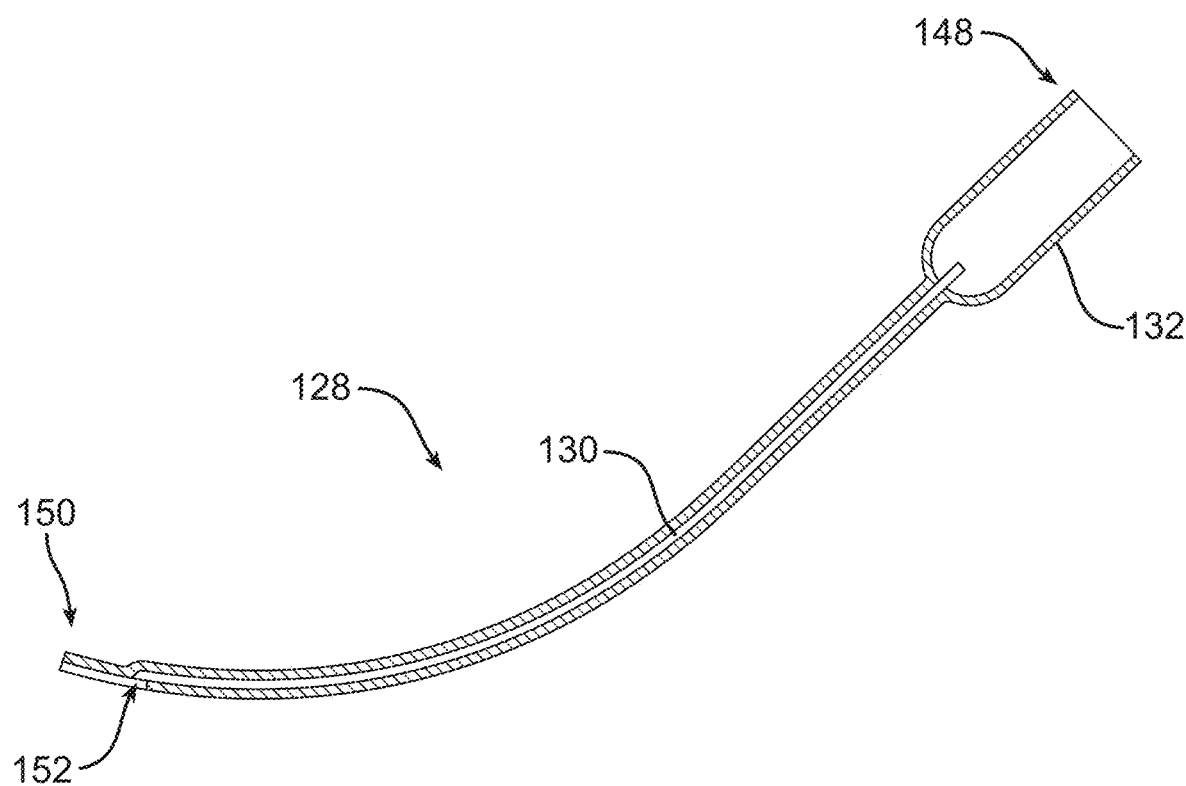
FIG. 6A is a cross-sectional view of the protective cover shown in FIGS. 5A and 5B.
Figure 6B:
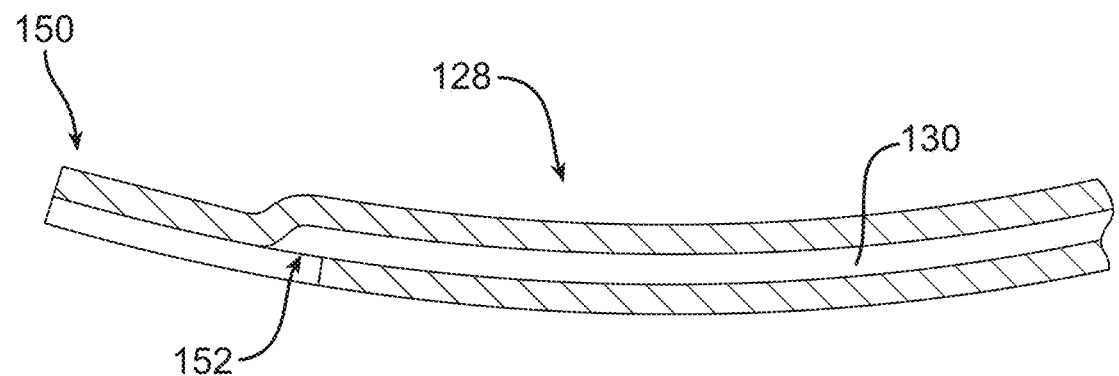
FIG. 6B is a magnified cross-sectional view of a distal end of the protective cover shown in FIG. 6A.

Referring to FIGS. 6A and 6B, in one embodiment, the protective cover 128 preferably has a proximal end 148 and a distal end 150. The syringe barrel connector 132 is adapted to be in fluid communication with the dispensing openings at the distal ends of the respective first and second syringe barrels 120, 122 (FIG. 1). The protective cover 128 preferably includes the sealant dispensing channel 130 that extends along the length of the protective cover. The sealant dispensing channel 130 preferably has a proximal end in fluid communication with the syringe barrel connector 132 and a distal end in fluid communication with the sealant dispensing opening 152 (FIG. 5B) so that the flowable, curable sealant may be dispensed at the distal end 150 of the protective cover 128.

Figure 7A:
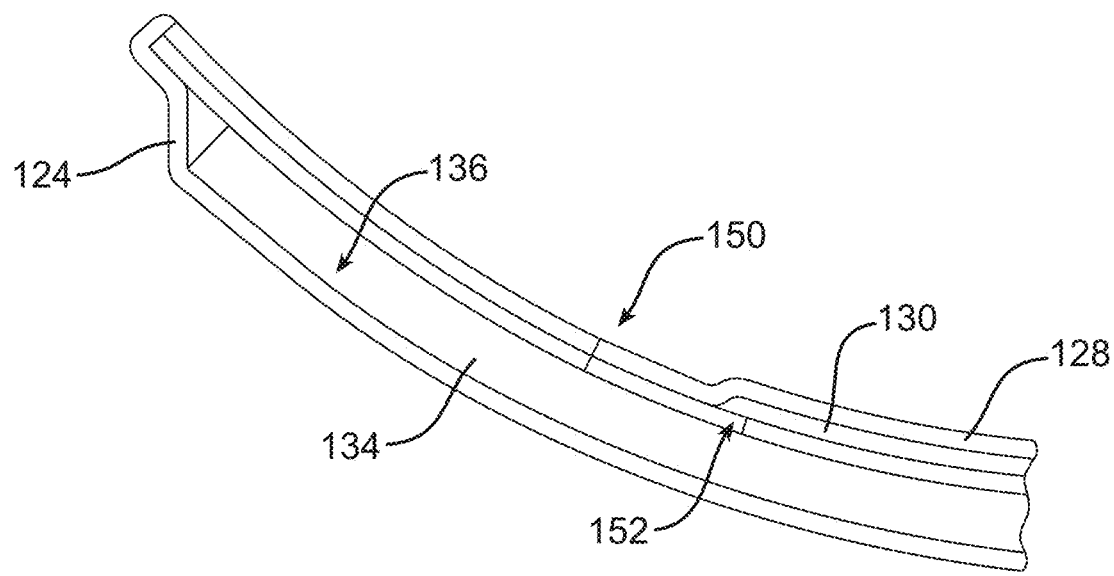
FIG. 7A shows a distal end of a sealant delivery device including a tray, an at least partially exposed matrix disposed within the tray, and a protective cover overlying a portion of the matrix.
Figure 7B:
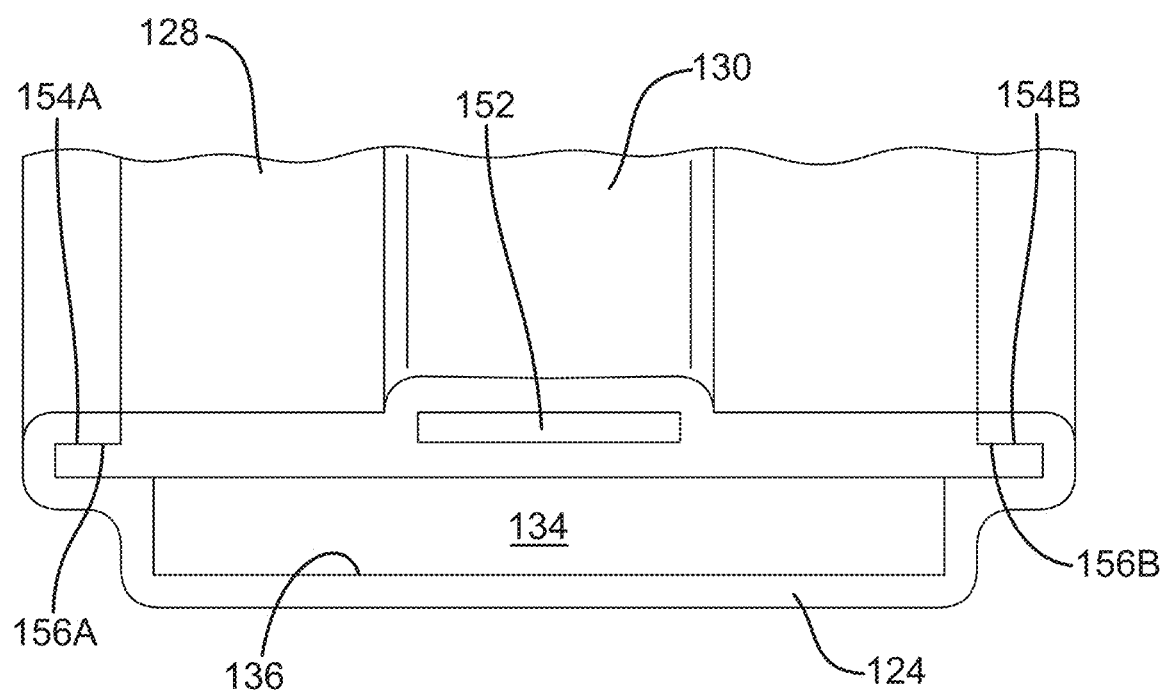
FIG. 7B is a cross-sectional view of the tray, the matrix, and the protective cover shown in FIG. 7A.

Referring to FIGS. 7A and 7B, in one embodiment, the matrix 134 is desirably disposed within the trough 136 of the tray 124. The protective cover 128 overlies both the trough 136 of the tray 124 and the matrix 134 disposed within the tray 124. The protective cover 128 preferably includes the sealant dispensing channel 130 that extends to the sealant dispensing opening 152 located adjacent the distal end 150 of the protective cover 128.

In FIG. 7B, the tray 124 is extended distally relative to the protective cover 128 so that the matrix 134 is at least partially exposed.

Referring to FIG. 7B, the protective cover 128 desirably includes the first and second lateral guide slots 154A, 154B that are configured to engage the respective lateral guide flanges 156A, 156B of the tray 124 for guiding the sliding movement of the tray 124 relative to the protective cover 128.

Figure 8A:
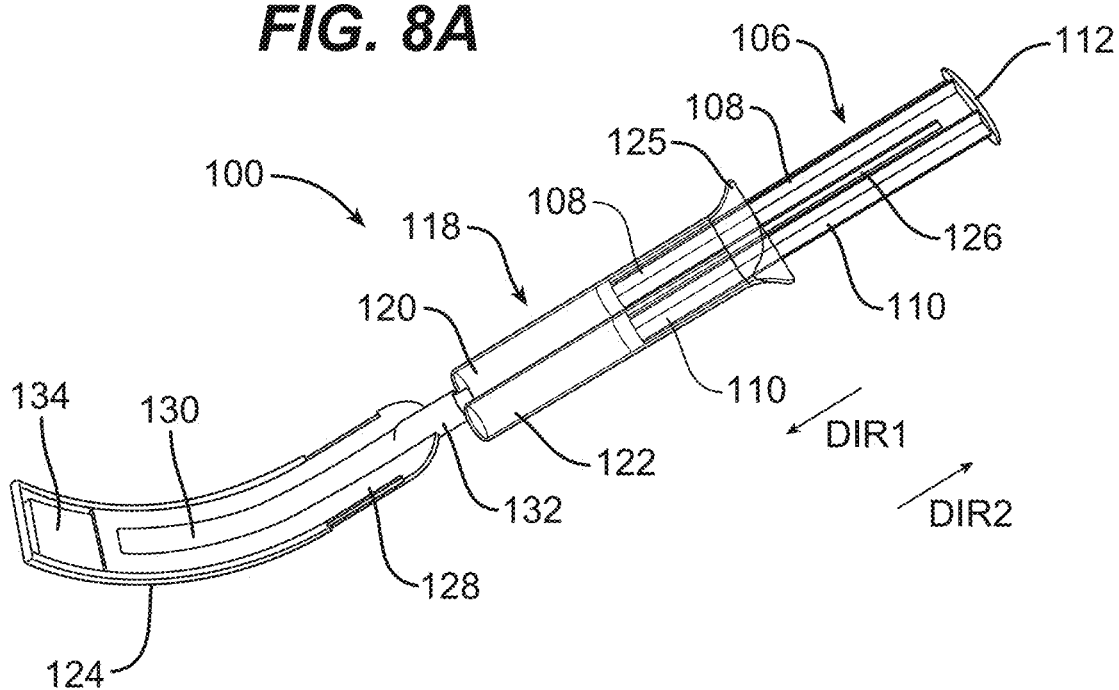
FIG. 8A is a perspective view of a sealant delivery device including a tray, a matrix disposed within the tray, and a protective cover overlying the matrix and the tray, whereby the tray is in an at least partially extended position for exposing a portion of the matrix, in accordance with one embodiment of the present patent application.
Figure 8B:
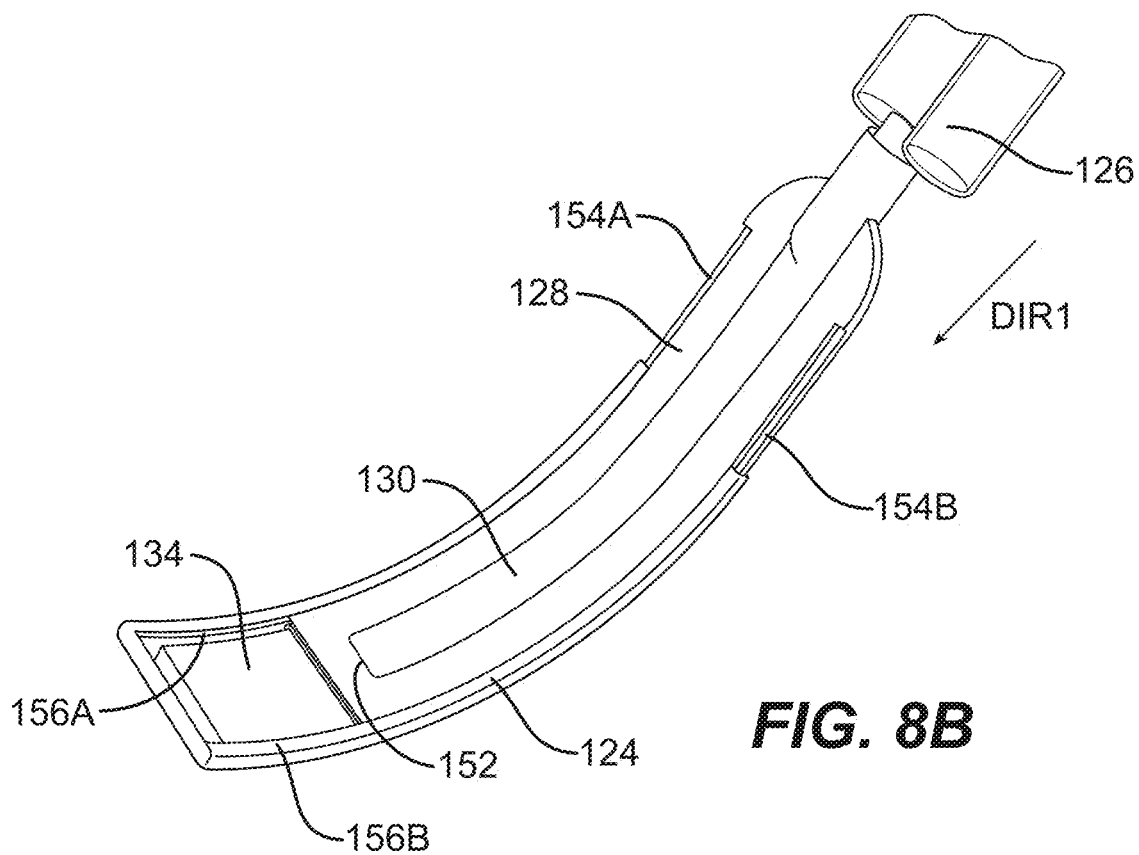
FIG. 8B is a magnified view of the distal end of the sealant delivery device shown in FIG. 8A.

Referring to FIGS. 8A and 8B, in one embodiment, the sealant delivery device 100 may be utilized during a surgical procedure for protecting the matrix 134 from surrounding tissue as the matrix is delivered to target tissue, expressing a sealant onto the matrix once the sealant has been delivered to the target tissue, exposing the matrix to the target tissue as the sealant is expressed onto the matrix, applying the matrix that has been infused with the expressed sealant onto the target tissue, and pressing the matrix with the infused sealant onto the target tissue for sealing the target tissue (e.g., to stop bleeding).

In one embodiment, the thumb tab 112 of the dual barrel syringe 118 is depressed in the distal direction DIR1 for sliding the first and second plungers 108, 110 distally relative to the respective first and second syringe barrels 120, 122. As the first and second plungers 108, 110 move distally, the first and second plungers 108, 110 force the first and second parts of the sealant composition from the distal ends of the respective first and second syringe barrels and into the syringe barrel connector 132. The first and second parts of the sealant are preferably mixed together within the syringe barrel connector 132 and the sealant mixture is then forced into the sealant dispensing channel 130 of the protective cover 128 for being dispensed from the distal end of the sealant dispensing channel and onto the matrix 134. In one embodiment, as the thumb tab 112 is advanced in the distal direction DIR1, the thumb tab engages the proximal end 138 of the push rod 126 for moving the push rod 126 in the distal direction DIR1.

Figure 8C:
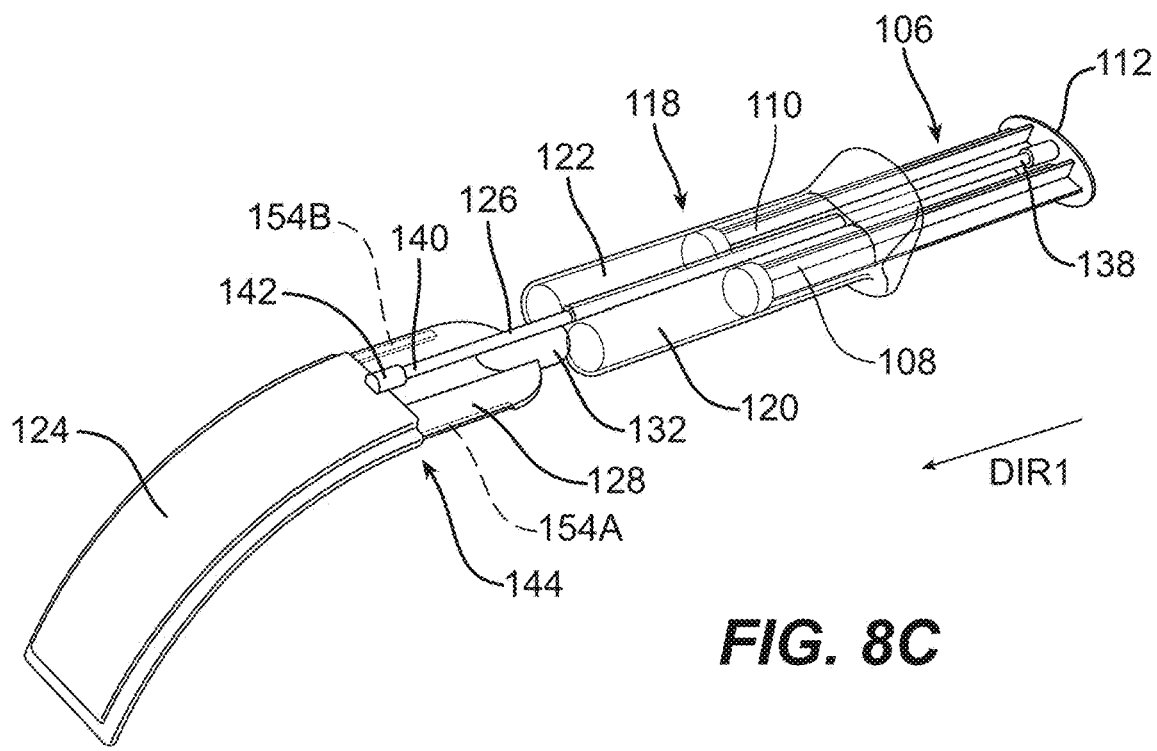
FIG. 8C is a perspective view of an underside of the sealant delivery device shown in FIGS. 8A and 8B.
Figure 8D:
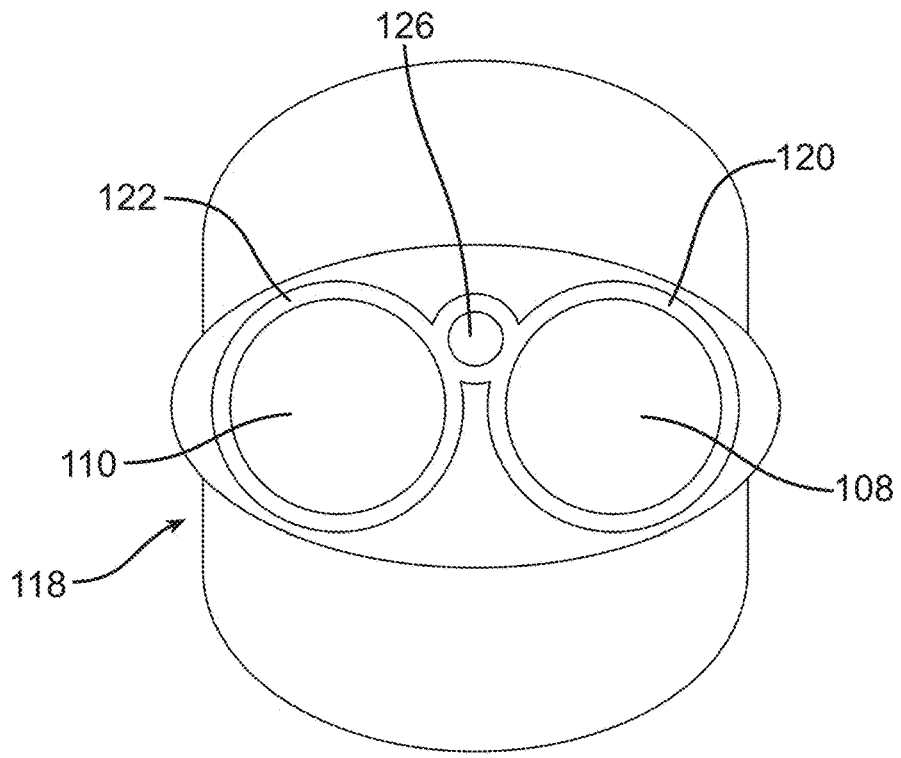
FIG. 8D is a cross-sectional view of the sealant delivery device shown in FIG. 8C.

Referring to FIGS. 8C and 8D, in one embodiment, the push rod 126 preferably extends between the first and second syringe barrels 120, 122 of the dual barrel syringe 118. In one embodiment, the push rod 126 preferably has a proximal end 138 that is connected with the thumb tab 112 of the double plunger 106 and a distal end 140 that is connected with the push rod connector 142 located at the proximal end 144 of the tray 124.

In one embodiment, as the push rod 126 is extended in the distal direction DIR1, the distal end 140 (FIG. 2) of the push rod 126 preferably engages the push rod connector 142 of the tray 124 for sliding the tray distally relative to the protective cover 128. As the tray 124 slides distally relative to the protective cover 128, a portion of the matrix 134 (FIG. 88) is exposed, Simultaneously, the sealant flowing through the sealant dispensing channel 130 of the protective cover 128 is dispensed onto the matrix 134 via the sealant dispensing opening 152 (FIGS. 6A and 7B) located at the distal end of the channel. The sliding movement of the tray 124 relative to the protective cover 128 is guided by the engagement of the laterally extending guide flanges 156A, 156B (FIG. 7B) of the tray 124 with the first and second laterally extending guide slots 154A, 154B of the protective cover 128.

In one embodiment, as the thumb tab 112 is pushed in the distal direction DIR1, the thumb tab forces the push rod 126 to also move in the distal direction, which, in turn, slides the tray 124 distally relative to the protective cover 128 for exposing the matrix 134 (FIG. 8B). Thus, in one embodiment, the double plunger 106, the push rod 126, and the tray 124 are adapted to move together simultaneously relative to the protective cover 128, the syringe barrel connector 132 and the dual barrel syringe 118.

In one embodiment, as the push rod 126 forces the tray 124 to slide distally relative to the protective cover 128, the first and second parts of the sealant disposed within the first and second syringe barrels 120, 122 are forced into the syringe barrel connector 132 by the first and second plungers 108, 110 of the double plunger 106.

Figure 9A:
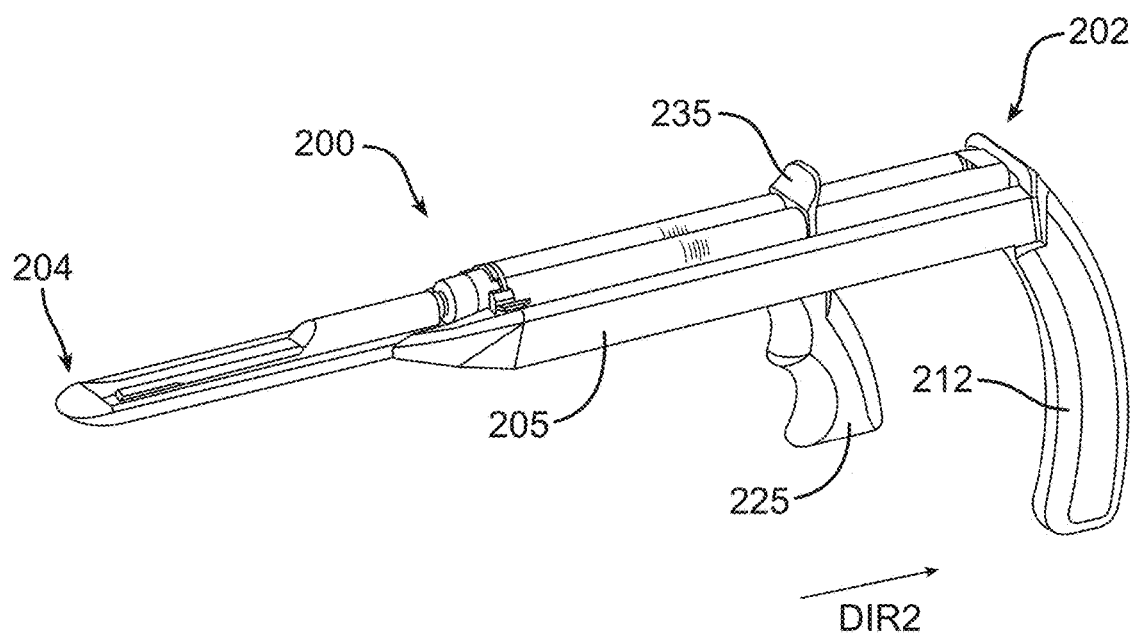
FIG. 9A is a perspective view a sealant delivery device including a handle and a trigger, in accordance with one embodiment of the present patent application.
Figure 9B:
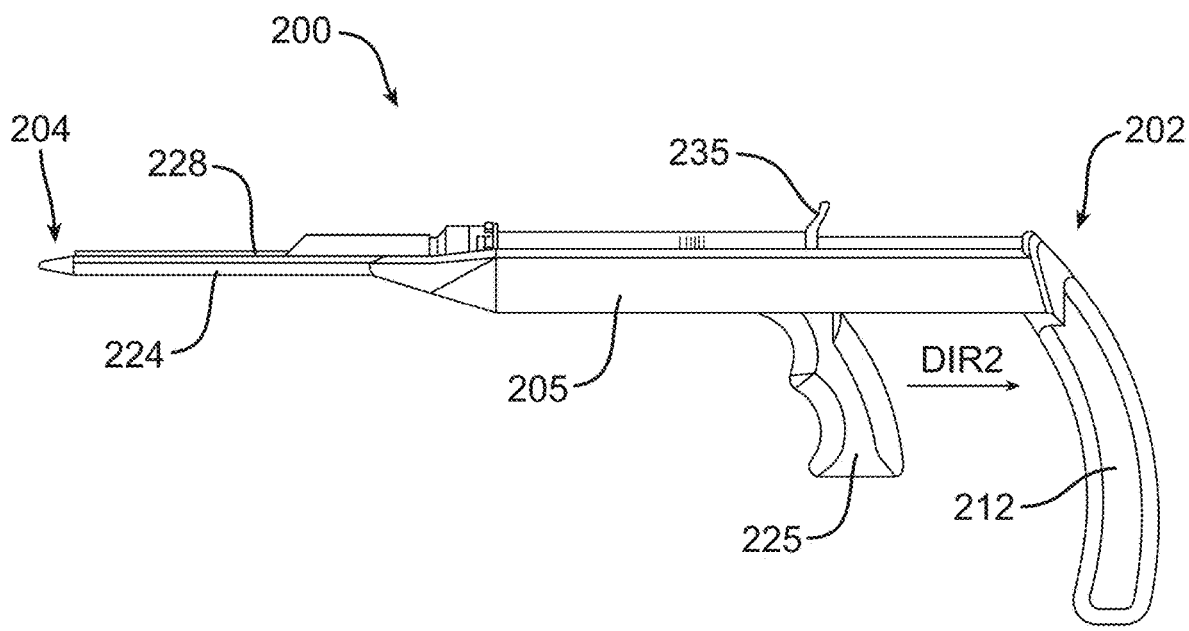
FIG. 9B is a side view of the sealant delivery device shown in FIG. 9A.

Referring to FIGS. 9A and 9B, in one embodiment, a sealant delivery device 200 may be activated using an actuator such as a trigger 225. In one embodiment, the sealant delivery device 200 preferably has a proximal end 202 and a distal end 204, the latter being configured for being advanced to target tissue for delivering a matrix to the target tissue. In one embodiment, the sealant delivery device 200 preferably includes a housing 205 having a handle 212 and the trigger 225 that is adapted for being squeezed in a proximal direction DIR2 toward the handle 212 for simultaneously exposing a matrix at the distal end 204 of the sealant delivery device 200 and applying a sealant onto the matrix, whereupon the matrix with the infused sealant may be pressed against the target tissue for controlling bleeding.

In one embodiment, the sealant delivery device 200 preferably includes a matrix container including a tray 224 that is adapted to contain a matrix and a protective cover 228 that may be retracted toward the proximal end 202 of the sealant delivery device 200 for exposing the matrix disposed within the tray 224. In one embodiment, the protective cover 228 is preferably coupled with the trigger 225 so that the protective cover moves simultaneously with the trigger 225 as the trigger is squeezed proximally toward the handle 212. In one embodiment, the tray 224 remains stationary as the protective cover moves proximally relative to the tray for moving the matrix container into an opened position for exposing the matrix to the surrounding environment and/or target tissue.

Figure 10:
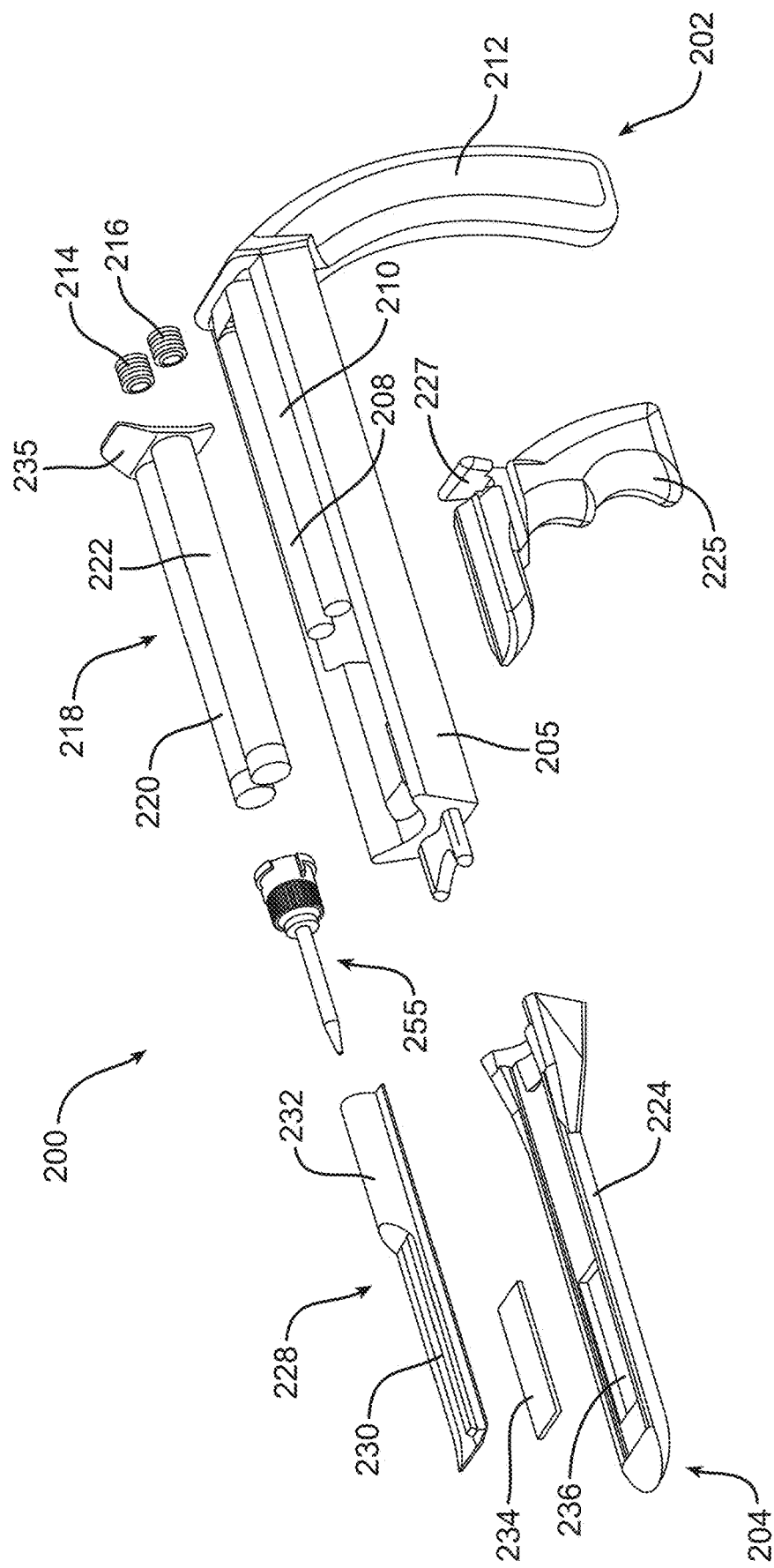
FIG. 10 is an exploded view of the sealant delivery device shown in FIGS. 9A and 9B including a handle having double plungers, a trigger, a dual barrel syringe, a mixing tip including a static mixer, a tray, a matrix, and a protective cover, in accordance with one embodiment of the present patent application.

Referring to FIGS. 9A-9B and 10, in one embodiment, the sealant delivery device 200 preferably includes the housing 205 having the handle 212 located at the proximal end 202 of the device 200. The housing 205 preferably includes a first plunger 208 and a second plunger 210 that extend toward the distal end 204 of the sealant delivery device. In one embodiment, the sealant delivery device 200 preferably includes a first piston 214 that is secured over a distal end of the first plunger 208 and a second piston 216 that is secured over the distal end of the second plunger 210.

In one embodiment the sealant delivery device 200 preferably includes a dual barrel syringe 218 having a first syringe barrel 220 and a second syringe barrel 222. In one embodiment, the first syringe barrel 220 is preferably adapted to receive a first part of a flowable, curable sealant and the second syringe barrel 222 is preferably adapted to receive a second part of the flowable, curable sealant. The first and second parts of the sealant are preferably mixed together to form the flowable sealant that applied onto the matrix 234.

In one embodiment, the proximal end of the dual barrel syringe 218 preferably includes a syringe barrel grip 235 that is preferably adapted to engage a connecting notch 245 provided on the trigger 225 for coupling the trigger 225 with the dual barrel syringe 218. The dual barrel syringe 218 and the trigger 225 move together as the trigger is squeezed.

In one embodiment, the sealant delivery device 200 preferably includes a mixing tip 255 that is connected with dispensing openings located at the distal ends of the respective first and second syringe barrels 220, 222. In one embodiment, the mixing tip 255 may include a static mixer that preferably enhances mixing of the first and second parts of the sealant as the first and second parts of the sealant flow through the length of the mixing tip 255.

In one embodiment, the sealant delivery device 200 preferably includes a tray 224 that is connected with the distal end of the housing 205. In one embodiment, the tray 224 preferably includes a trough 236 that is adapted to receive (e.g., seat) the matrix 234. The sealant delivery device 200 preferably includes the protective cover 228 that is adapted to overlie the tray 224 and the matrix 234 for protecting the matrix 234 as the distal end 204 of the sealant delivery device 200 is moved into position prior to deployment of the matrix 234 onto target tissue.

In one embodiment the protective cover 228 preferably includes a mixing tip connector 232 that is adapted to receive a distal end of the mixing tip 255 so that the flowable sealant, preferably after being mixed, may be directed into a sealant dispensing channel 230 of the protective cover 228.

Figure 11A:
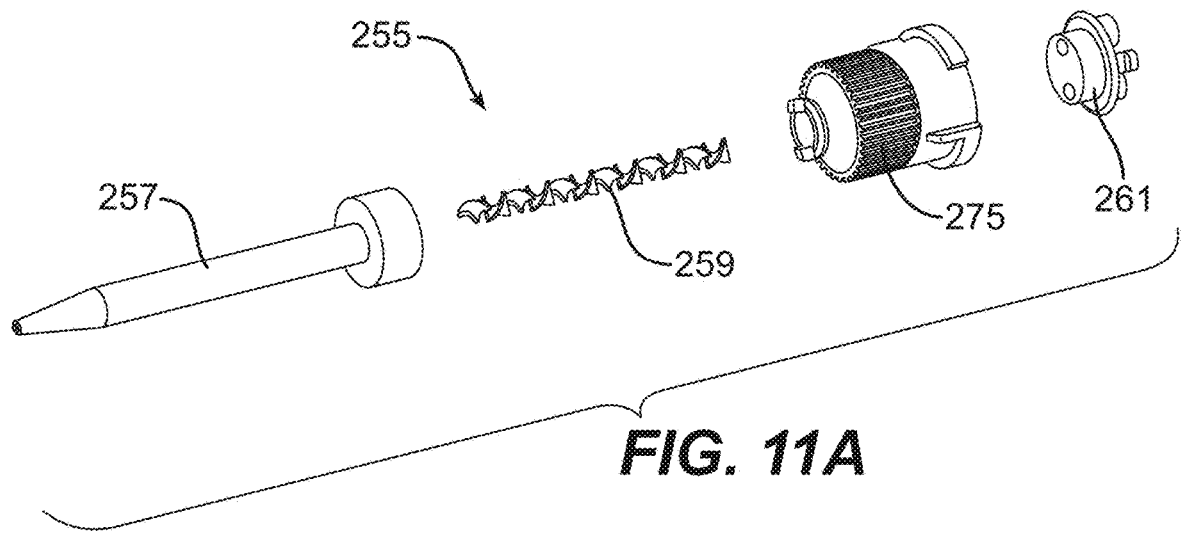
FIG. 11A is an exploded view of the mixing tip of the sealant delivery device shown in FIG. 10 including a sealant delivery tube, a static mixer, a syringe barrel connector, and a mixing tip manifold, in accordance with one embodiment of the present patent application.
Figure 11B:
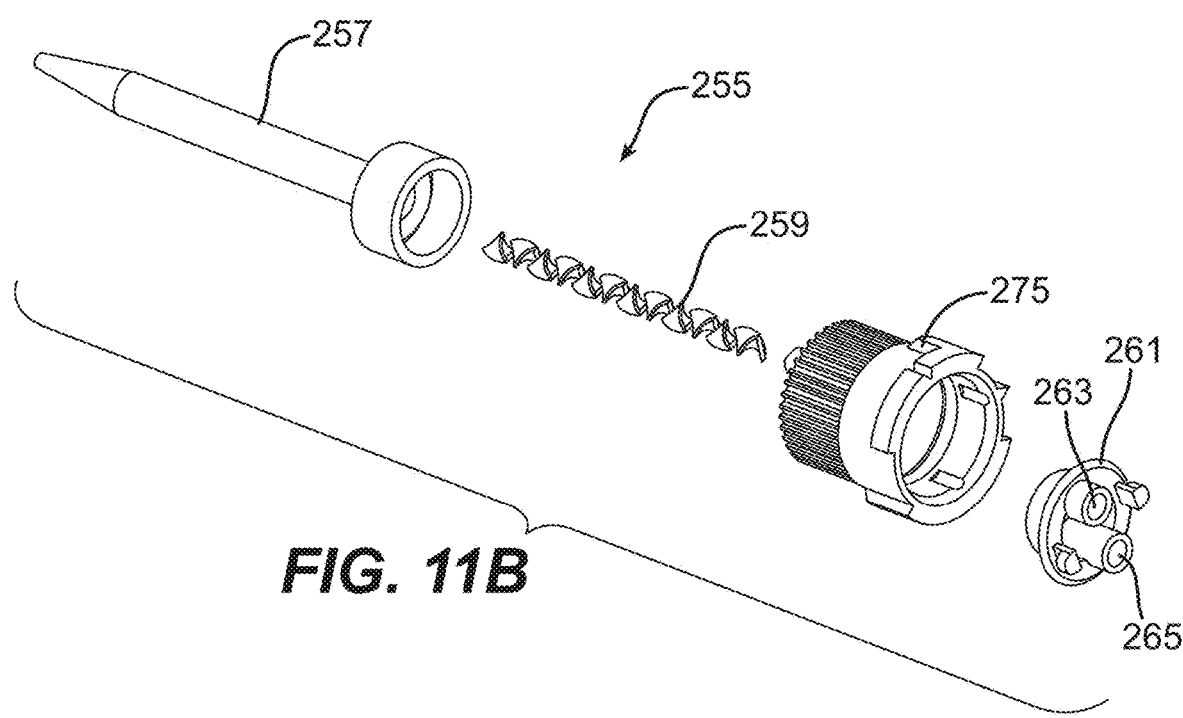
FIG. 11B is another exploded view of the mixing tip shown in FIG. 11A.

Referring to FIGS. 11A and 11B, in one embodiment, the mixing tip 255 preferably includes a sealant delivery tube 257 that is adapted to receive a static mixer 259, and a syringe barrel connector 275 that is adapted to connect a proximal end of the mixing tip 255 with the distal ends of the respective first and second syringe barrels 220, 222. In one embodiment, the mixing tip 255 preferably includes a mixing tip manifold 261 that is inserted into an opening at a proximal side of the syringe barrel connector 275. The mixing tip manifold 261 preferably has a first opening 263 that is in fluid communication with a dispensing opening located at the distal end of the first syringe barrel 220 (FIG. 10) and second fluid opening 265 that is preferably in fluid communication with a dispensing opening located at the distal end of the second syringe barrel 222. The mixing tip 255 including the static mixer 259 is preferably adapted for mixing together the first and second parts of the sealant as the sealant mixture passes along the length of the mixing tip 255.

The structural elements shown in FIGS. 11A and 11B disclose one embodiment for mixing a sealant. Those skilled in the art will recognize that there are other well-known systems, devices and methods for mixing sealants, and that those other well-known systems, devices and methods may be utilized in place of the structural elements shown in FIGS. 11A and 11B.

Figure 12A:
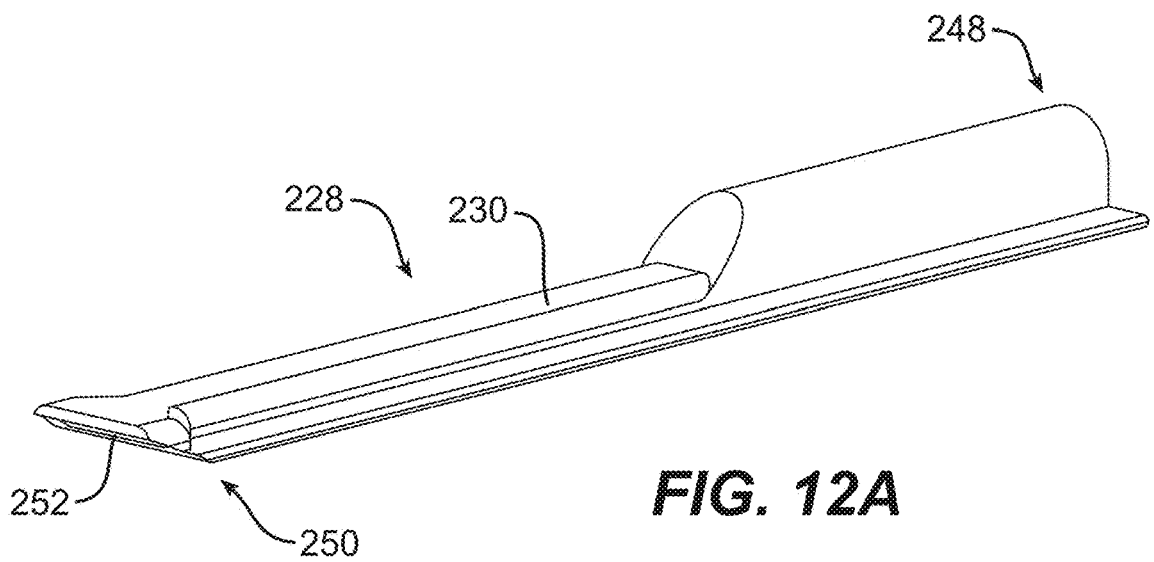
FIG. 12A is a perspective view of a top side of the protective cover of the sealant delivery device shown in FIG. 10, in accordance with one embodiment of the present patent application.
Figure 12B:
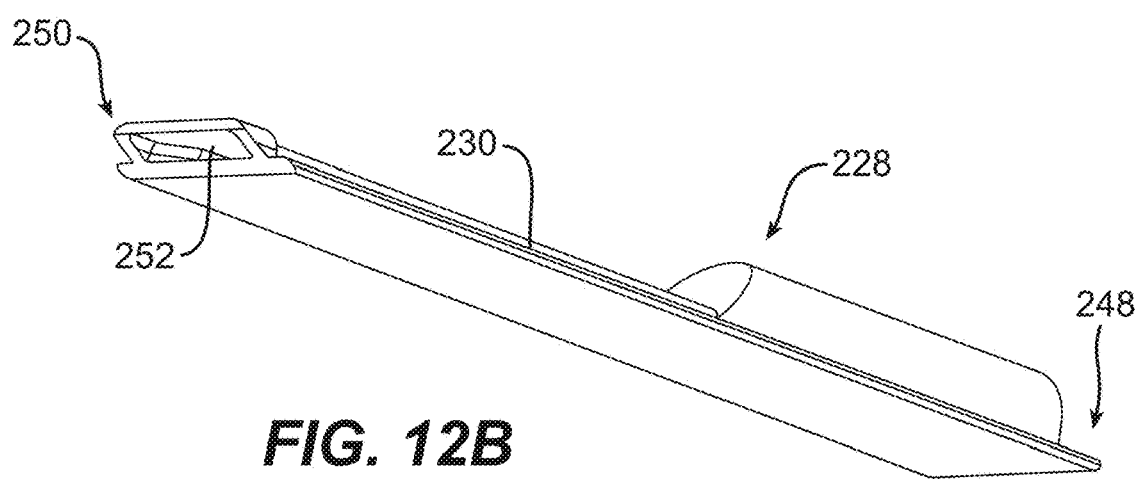
FIG. 12B is a perspective view of an underside of the protective cover shown in FIG. 12A.
Figure 12C:
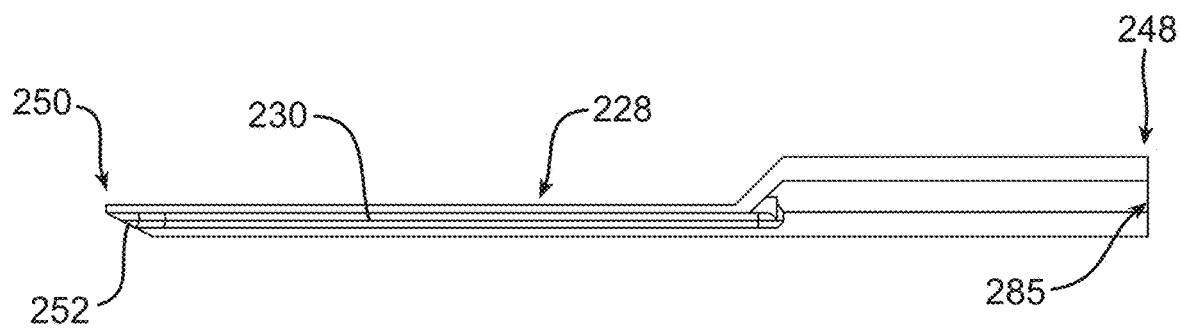
FIG. 12C is a cross-sectional view of the protective cover shown in FIGS. 12A and 12B.

Referring to FIGS. 12A-12C, in one embodiment, the protective cover 228 preferably has a proximal end 248 and a distal end 250. In one embodiment, the protective cover 228 preferably includes a sealant dispensing channel 230 that extends along the length of the protective cover 228 between the proximal end 248 and the distal end 250 thereof. In one embodiment, the protective cover 228 preferably includes a dispensing opening 252 located adjacent the distal end 250 of the protective cover 228. In one embodiment, a flowable sealant that is directed into an inlet opening 285 (FIG. 120) located at the proximal end 248 of the protective cover 228 is directed toward the sealant dispensing channel 230 and the sealant dispensing opening 252 at the distal end 250 of the protective cover 228 for being dispensed onto the matrix 234 disposed within the tray 224 of the sealant delivery device 200 (FIG. 10).

Figure 13A:
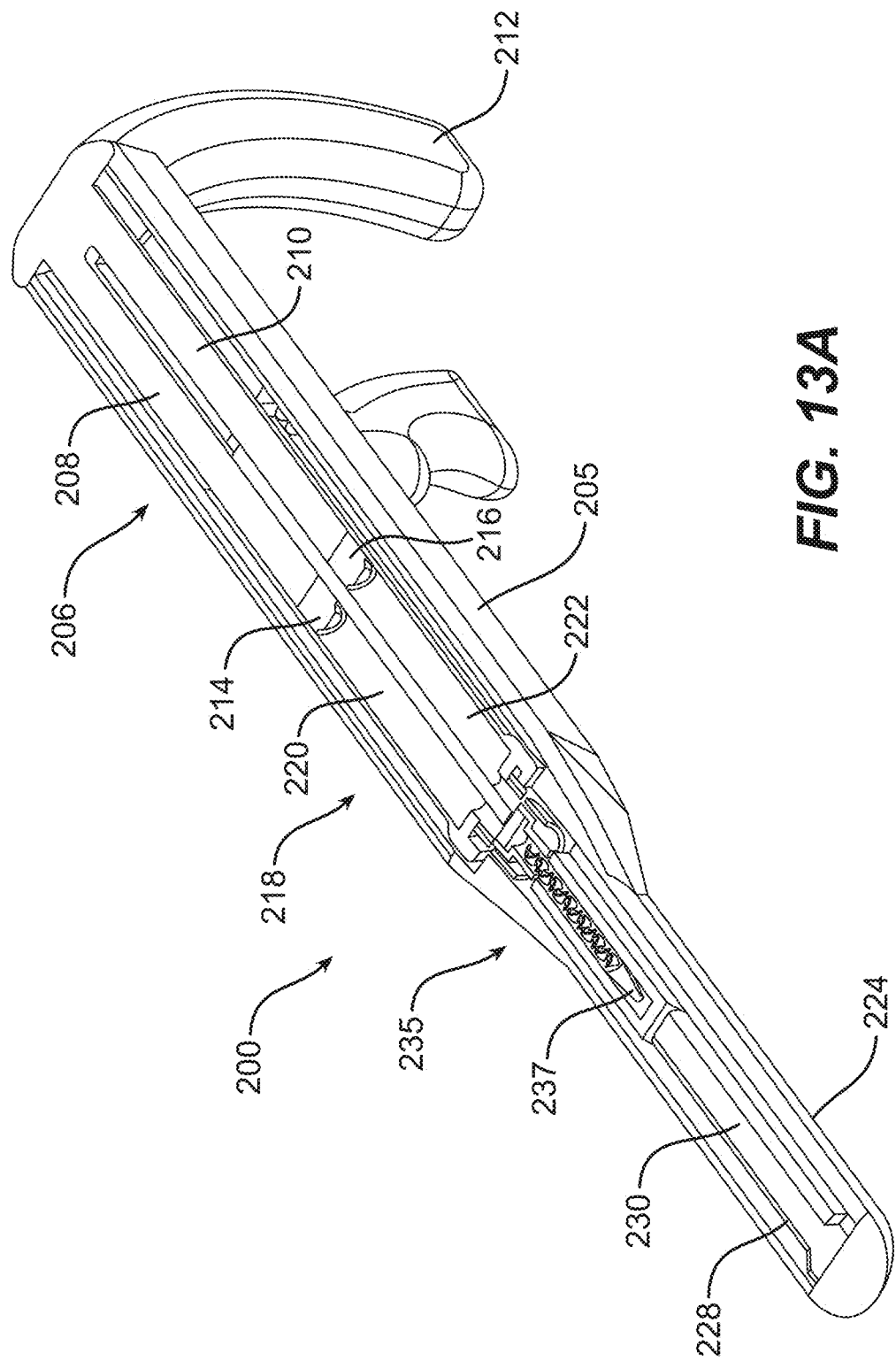
FIG. 13A is a cross-sectional view of the sealant delivery device shown in FIGS. 9A-9B and 10.

Referring to FIGS. 13A and 13B, in one embodiment, the sealant delivery device 200 preferably includes the housing 205 having the handle 212. The tray 224 is secured to the distal end of the housing 205. The sealant delivery device 200 includes the double plunger 206 having the first plunger 208 and the second plunger 210. The first piston 214 is secured to the distal end of the first plunger 208 and the second piston 216 is secured to the distal end of the second plunger 210.

In one embodiment, the sealant delivery device 100 preferably includes the dual barrel syringe 218 disposed within the housing 205. The dual barrel syringe 218 preferably includes the first syringe barrel 220 and the second syringe barrel 222. In one embodiment, the first plunger 208 and the first piston 214 are preferably disposed within the first syringe barrel 220. In one embodiment, the second plunger 210 and the second piston 216 are preferably disposed within the second syringe barrel 222. In one embodiment, dispensing openings located at the distal ends of the respective first and second syringe barrels 220, 222 are preferably in fluid communication with a proximal end of the mixing tip 235. The distal end of the sealant delivery tube 257 (FIG. 11A) of the mixing tip 255 is preferably in fluid communication with the sealant dispensing channel 230 of the protective cover 228. In FIGS. 13A and 13B, the protective cover 228 is preferably in an extended position relative to the tray 228 for covering and protecting the matrix 234 (FIG. 10) disposed within the trough of the tray 224.

Referring to FIG. 14, in one embodiment, the matrix 234 is preferably disposed within the trough 236 of the tray 224. The protective cover 228 preferably overlies the matrix 234 and the tray 224 for protecting the matrix 234 within the tray. The distal end of the sealant delivery tube 257 of the mixing tip 255 is preferably in fluid communication with the mixing tip connector 232 at the proximal end of the protective cover 228. As the trigger 225 (FIG. 9A) is squeezed, the flowable sealant mixture that passes through the static mixer 259 of the mixing tip 255 is preferably directed into the sealant dispensing channel 230 of the protective cover 228 for being dispensed onto the matrix 234 as the protective cover 228 is retracted in the proximal direction DIR2 relative to the tray 224 and the matrix 234. In one embodiment, the tray 224 and the matrix 234 remain stationary as the protective cover 228 is retracted relative to the tray.

Figure 15:
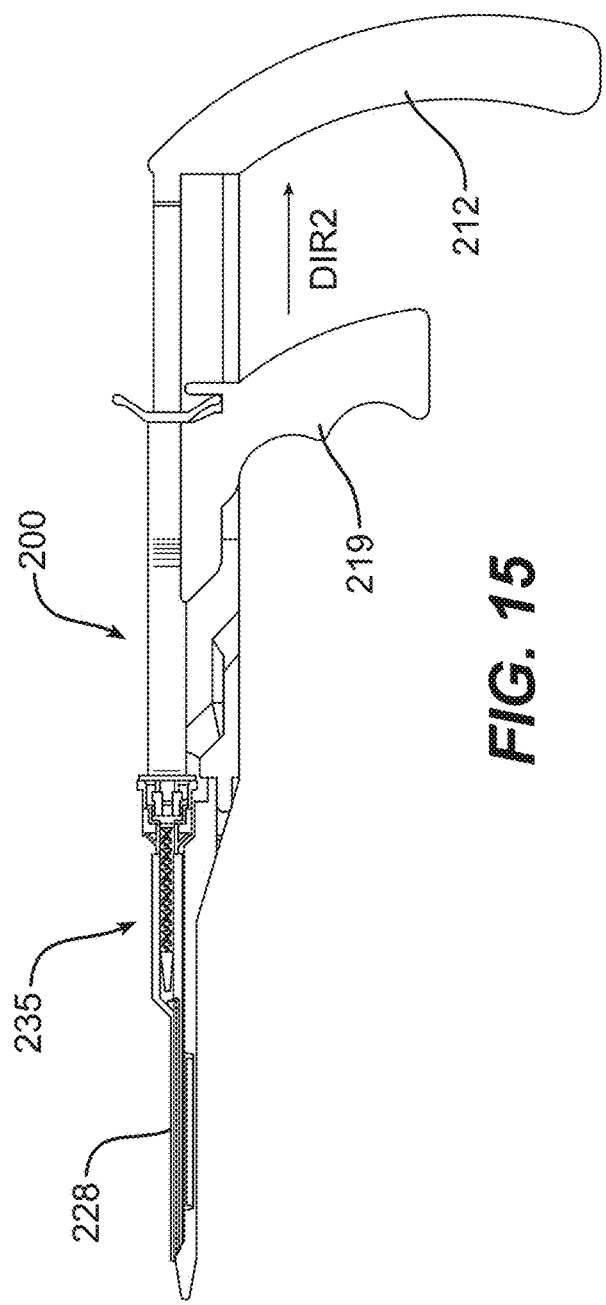
FIG. 15 is a side elevation view of a sealant delivery device prior to commencement of sequence for deploying a matrix, in accordance with one embodiment of the present patent application.
Figure 16:
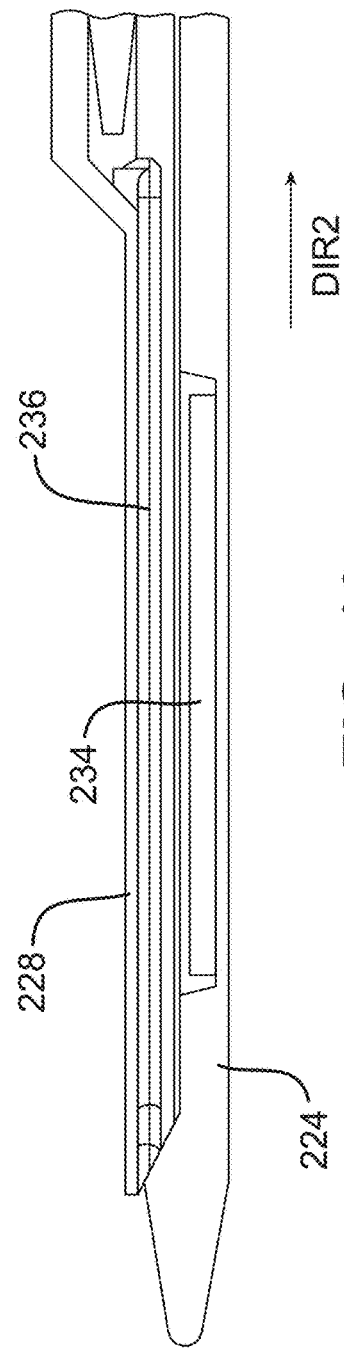
FIG. 16 is a magnified view of a distal end of the sealant delivery device shown in FIG. 15 including the tray, the matrix, and the protective cover overlying the matrix and the tray.
Figure 17:
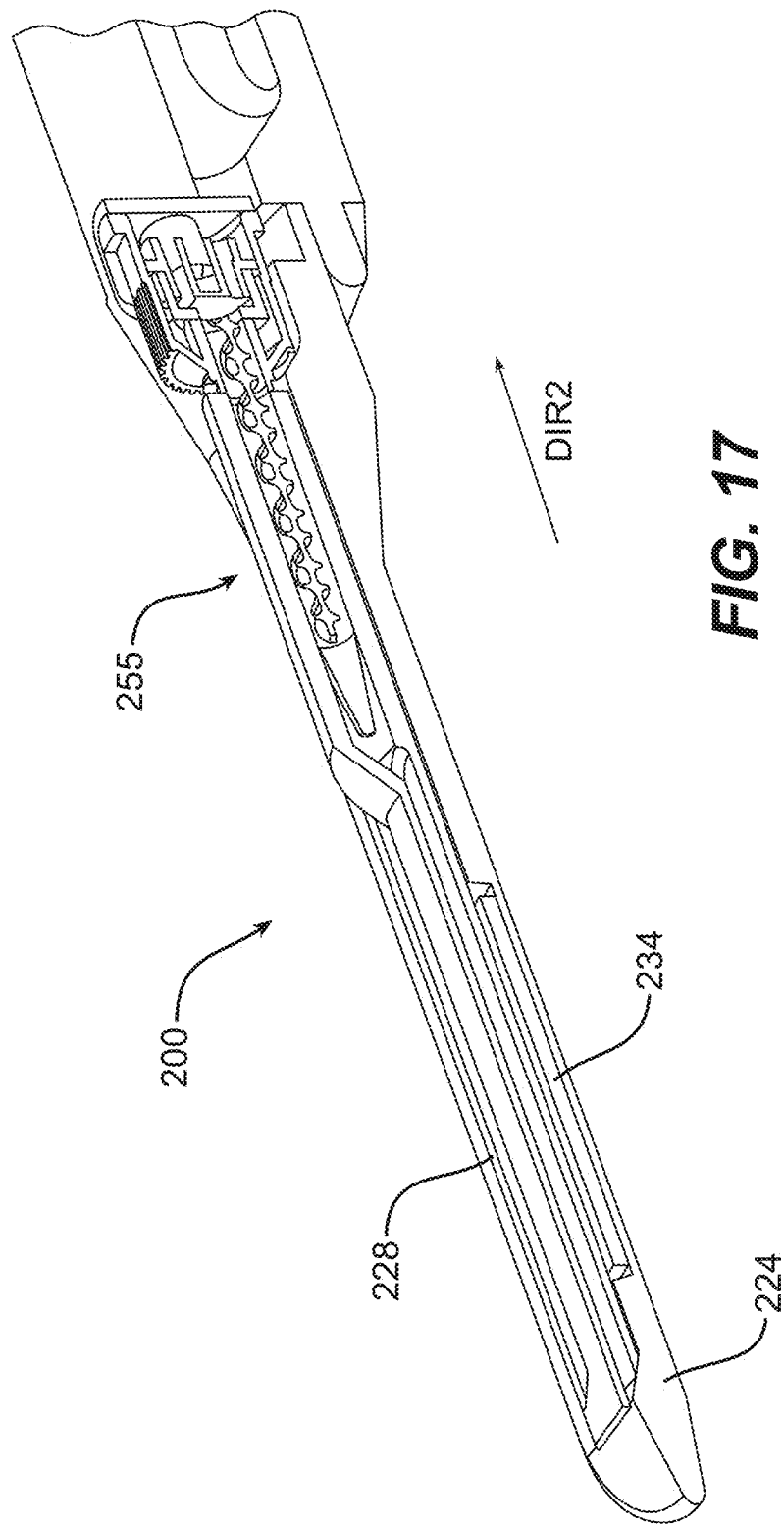
FIG. 17 is a perspective, cross-sectional view of the distal end of the sealant delivery device shown in FIGS. 15 and 16.

Referring to FIGS. 15-17, in one embodiment, with the trigger 225 in an extended position relative to the grip 212 of the housing 205, the protective cover 228 is in a fully extended position for covering the matrix 234 disposed within the trough 236 of the tray 224. Prior to the trigger 225 being squeezed in the proximal direction DIR2, the first and second parts of the sealant remain within the respective first and second syringe barrels and are not yet mixed together nor have the two parts of the sealant been directed into the mixing tip 255 (FIG. 17) of the sealant delivery device 200.

Referring to FIGS. 18 and 19, in one embodiment, as the trigger 225 is squeezed in the proximal direction DIR2 toward the handle 212, the trigger 225 pulls the grip 235 is located at the proximal end of the dual barrel syringe 218 in the proximal direction for forcing the first and second parts of the flowable sealant disposed within the respective first and second syringe barrels into the mixing tip 255 (FIG. 17), whereupon the two parts of the sealant are mixed together to form the sealant. Simultaneously, at the same time that the two parts of the sealant are mixed together, the protective cover 228, which is coupled with the trigger 225, is retracted in the proximal direction DIR2 for at least partially exposing the matrix 234 that is disposed within the trough 236 of the tray 224. As the protective cover 228 moves proximally in the direction DIR2 for uncovering the matrix, the sealant mixture preferably flows in the distal direction DIR1 through the sealant dispensing channel 230 of the protective cover 228 for being dispensed onto the matrix 234.

Figure 20A:
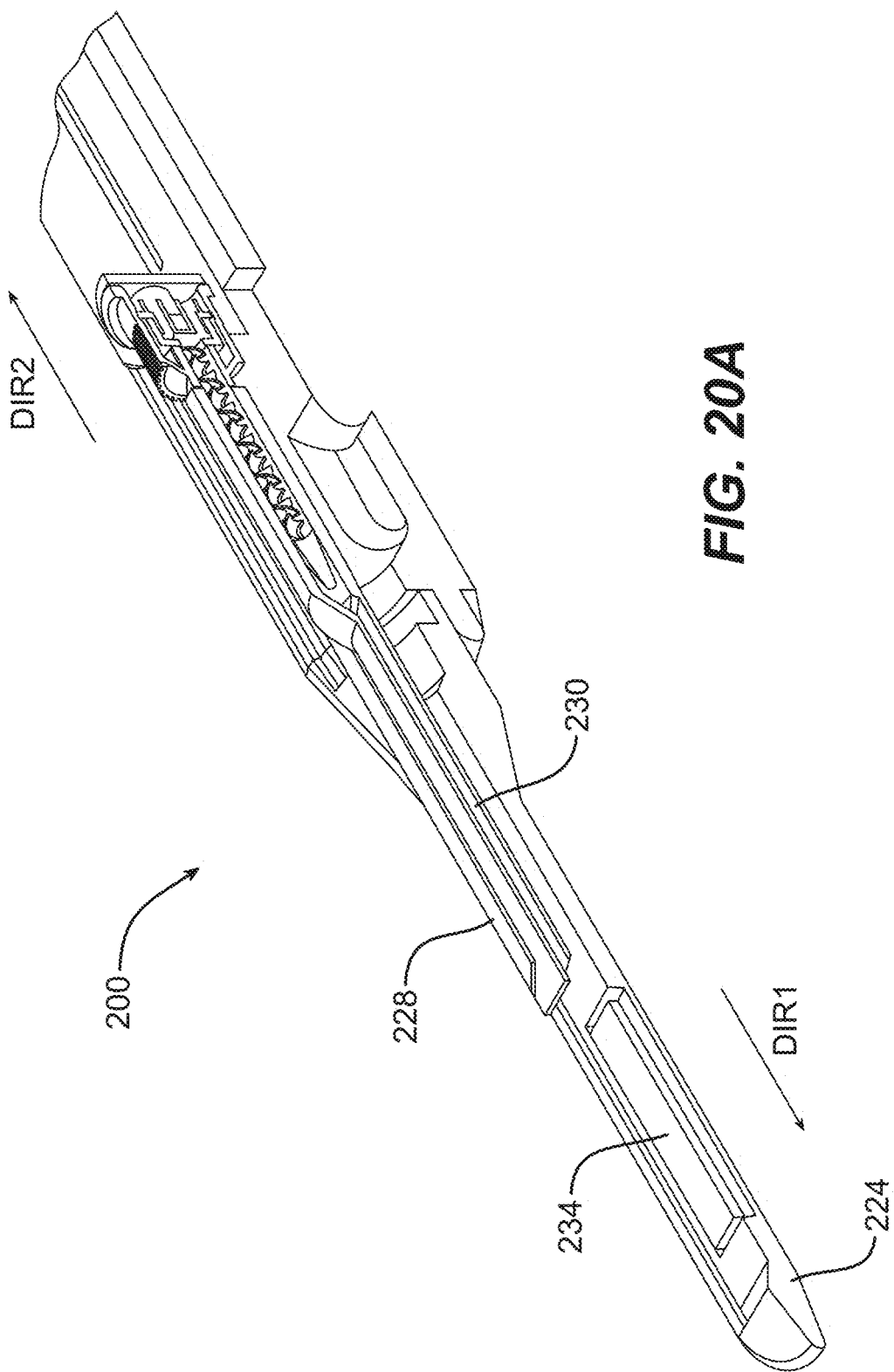
FIG. 20A is a perspective, cross-sectional view of the distal end of the sealant delivery device shown in FIGS. 18 and 19 with the protective cover in a fully retracted position for exposing the matrix that is disposed within the tray.
Figure 20B:
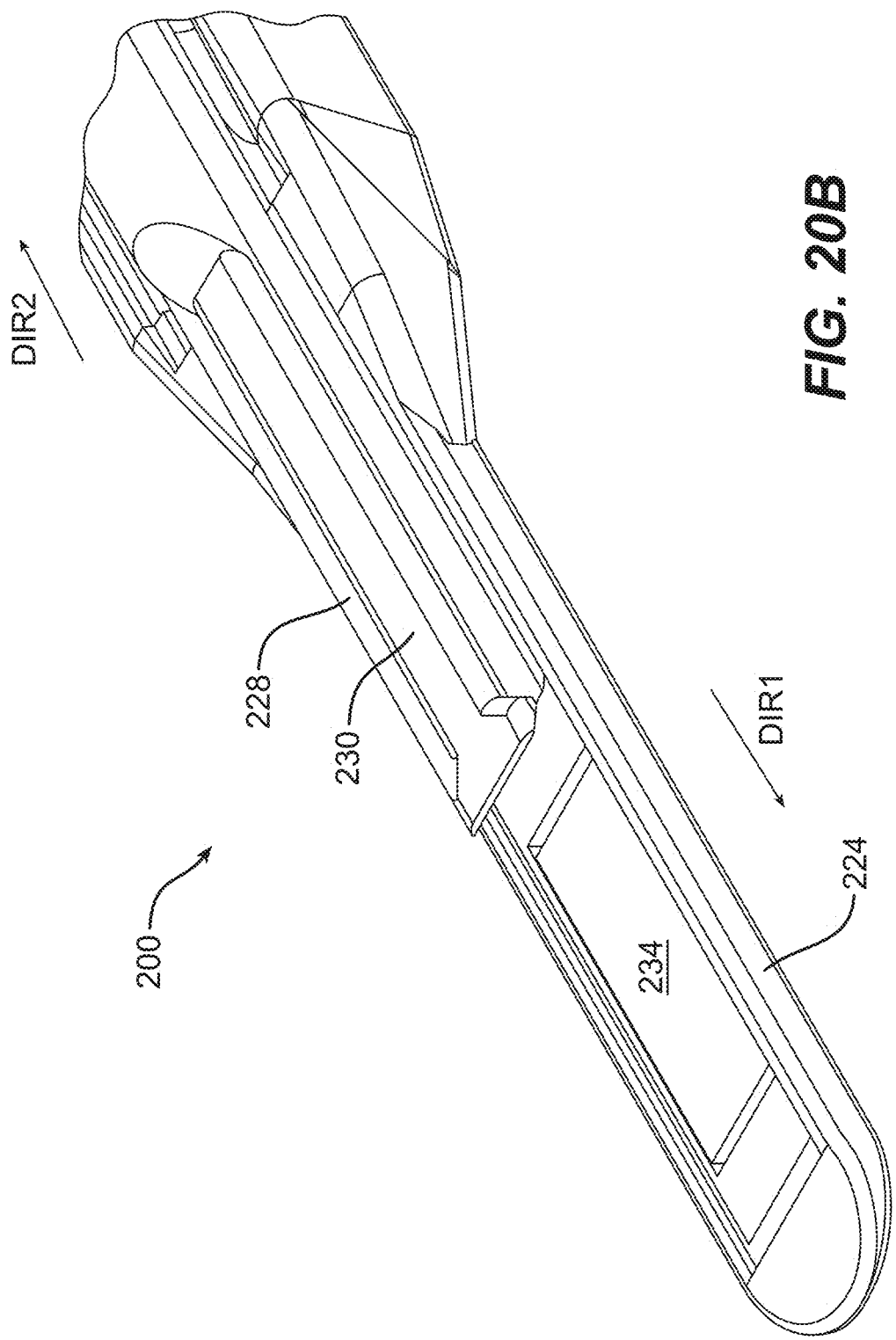
FIG. 20B is a magnified view of the distal end of the sealant delivery device shown in FIG. 20A.

Referring to FIGS. 20A and 20B, in one embodiment, with the protective cover 228 in a fully retracted position relative to the tray 224, the matrix 234, infused with the sealant, is exposed so that it may be applied onto target tissue for stopping and/or controlling bleeding. As the protective cover 228 slides in the proximal direction DI R2, the flowable sealant moves through the sealant dispensing channel 230 in the distal direction DIR1 for being dispensed onto the matrix 234.

Figure 21A:
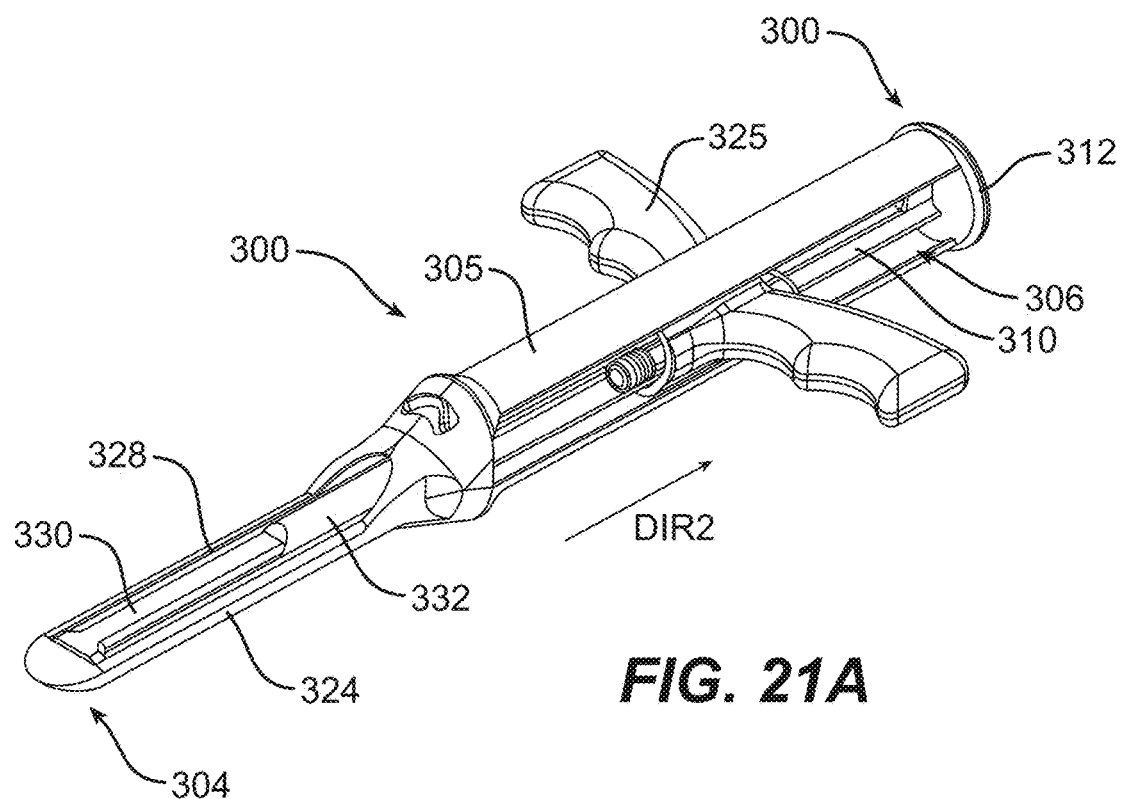
FIG. 21A is a perspective view of a sealant delivery device, in accordance with one embodiment of the present patent application.
Figure 21B:
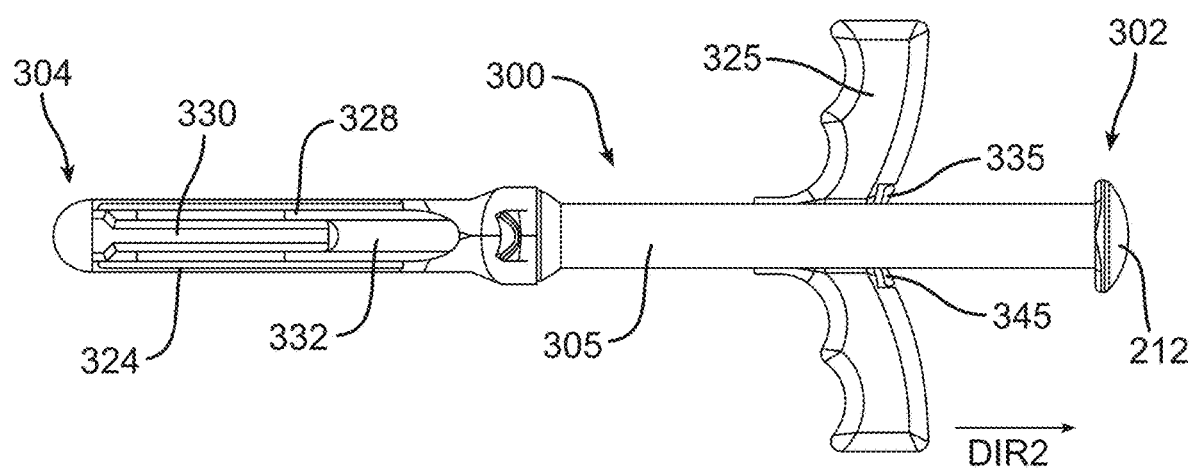
FIG. 21B is a top view of the sealant delivery device shown in FIG. 21A.

Referring to FIGS. 21A and 21B, in one embodiment, a sealant delivery device 300 may be activated using an actuator 324. In one embodiment, the sealant delivery device 300 preferably has a proximal end 302 and a distal end 304, the latter being configured for being advanced to target tissue for delivering a matrix to the target tissue. In one embodiment, the sealant delivery device 300 preferably includes a housing 305 having a palm stop 312 and the actuator 325 that is adapted for being pulled in a proximal direction DIR2 toward the palm stop 312 for simultaneously exposing a matrix at the distal end 304 of the sealant delivery device 300 and expressing a curable sealant onto the matrix.

In one embodiment, the sealant delivery device 300 preferably includes a tray 324 that is adapted to contain a matrix and a protective cover 328 that may be retracted toward the proximal end 302 of the sealant delivery device 300 for exposing the matrix disposed within the tray 324. In one embodiment, the protective cover 328 is preferably coupled with the actuator 325 so that the protective cover moves simultaneously with the actuator 325 as the actuator is squeezed and/or pulled proximally toward the palm stop 312.

Figure 22:
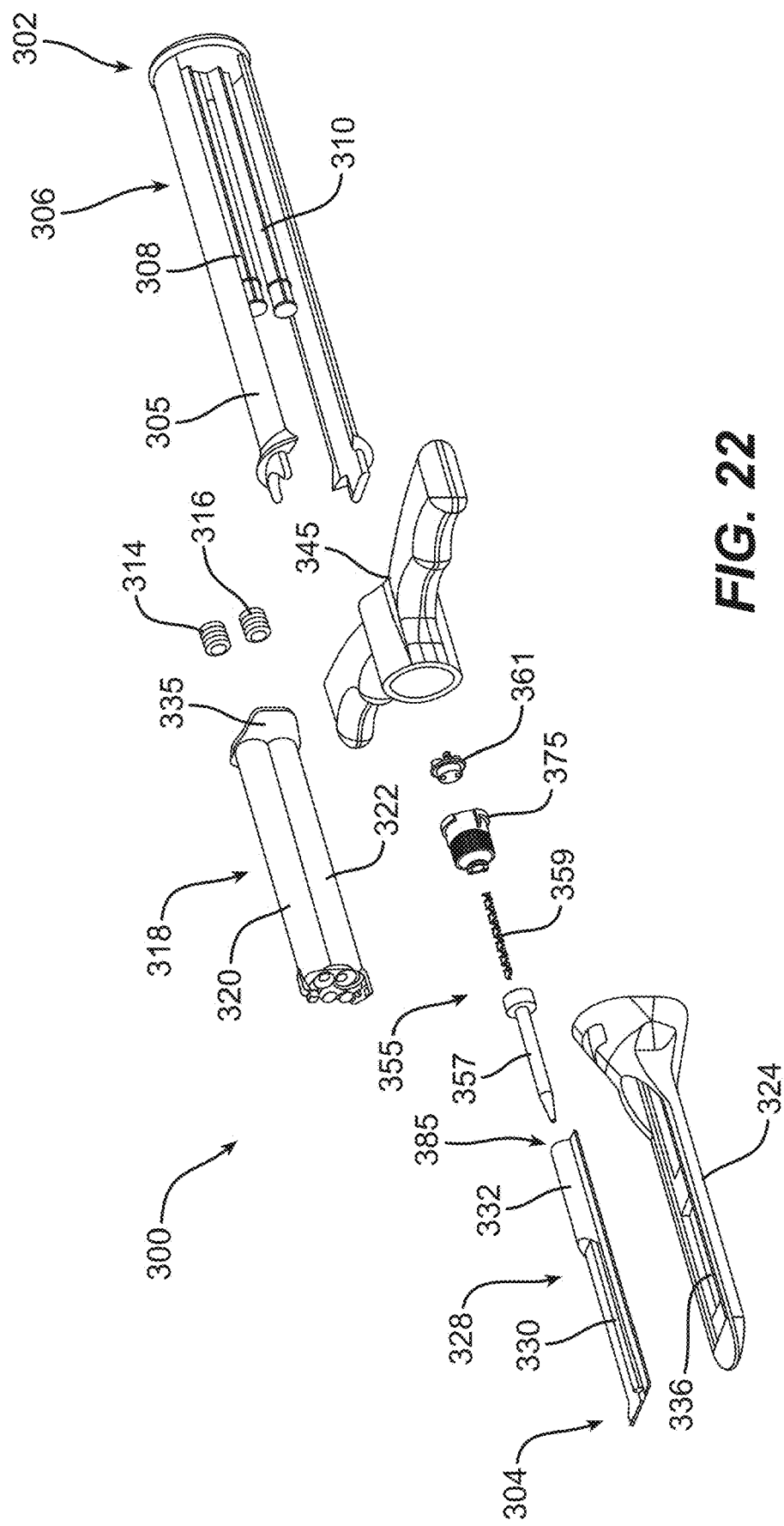
FIG. 22 is an exploded view of the sealant delivery device shown in FIGS. 21A and 21B including a housing having a double plunger, a dual barrel syringe, an actuator, a mixing tip, a tray configured to hold a matrix, and a protective cover, in accordance with one embodiment of the present patent application.

Referring to FIGS. 21A-21B and 22, in one embodiment, the sealant delivery device 300 preferably includes the housing 305 having a double plunger 306 including a first plunger 308 and a second plunger 310 that extend toward the distal end 304 of the sealant delivery device. In one embodiment, the sealant delivery device 300 preferably includes a first piston 314 that is secured over a distal end of the first plunger 308 and a second piston 316 that is secured over the distal end of the second plunger 310.

Referring to FIG. 22, in one embodiment, the sealant delivery device 200 preferably includes a dual barrel syringe 318 having a first syringe barrel 320 and a second syringe barrel 322. In one embodiment, the first syringe barrel 320 is preferably adapted to receive a first part of a flowable, curable sealant and the second syringe barrel 322 is preferably adapted to receive a second part of the flowable, curable sealant. The first and second parts of the sealant are preferably mixed together to form the flowable, curable sealant that applied onto the matrix 334 (FIG. 23B) for controlling and/or stopping bleeding of the target tissue.

In one embodiment, the proximal end of the dual barrel syringe 318 preferably includes a syringe barrel grip 335 that is preferably adapted to engage a connecting notch 345 provided on a proximal side of the actuator 325 for coupling the actuator 325 with the dual barrel syringe 318.

In one embodiment, the sealant delivery device 200 preferably includes a mixing tip 355 that is in fluid communication with dispensing openings located at the distal ends of the respective first and second syringe barrels 320, 322. In one embodiment, the mixing tip 355 may include a static mixer 359 that preferably enhances mixing of the first and second parts of the sealant as the first and second parts of the sealant flow through the length of the mixing tip 355.

In one embodiment, the sealant delivery device 300 preferably includes a tray 324 that is connected with the distal end of the housing 305. In one embodiment, the tray 324 preferably includes a trough 336 that is adapted to receive (e.g., seat) the matrix 334 (FIG. 23B). The sealant delivery device 300 preferably includes the protective cover 328 that is adapted to overlie the tray 324 and the matrix 334 (FIG. 23B) for protecting the matrix as the distal end 304 of the sealant delivery device 300 is moved into position prior to deployment of the matrix 334 (FIG. 23B) onto target tissue.

In one embodiment the protective cover 328 preferably includes a mixing tip connector 332 that is adapted to receive a distal end of the mixing tip 355 so that the flowable sealant may be directed into a sealant dispensing channel 330 of the protective cover 328.

Referring to FIG. 22, in one embodiment, the mixing tip 355 preferably includes a sealant delivery tube 357 that is adapted to receive the static mixer 359, and a syringe barrel connector 353 that is adapted to connect a proximal end of the mixing tip 355 with the distal ends of the respective first and second syringe barrels 320, 322. In one embodiment, the mixing tip 355 preferably includes a mixing tip manifold 361 that is inserted into an opening at a proximal side of the syringe barrel connector 375. The mixing tip manifold 361 preferably has a first opening that is in fluid communication with a dispensing opening located at the distal end of the first syringe barrel 320 and second fluid opening that is preferably in fluid communication with a dispensing opening located at the distal end of the second syringe barrel 322. The mixing tip 355 including the static mixer 359 is preferably adapted for mixing together the first and second parts of the sealant as the sealant mixture passes through the sealant delivery tube 357 and along the length of the mixing tip 355.

Figure 23A:
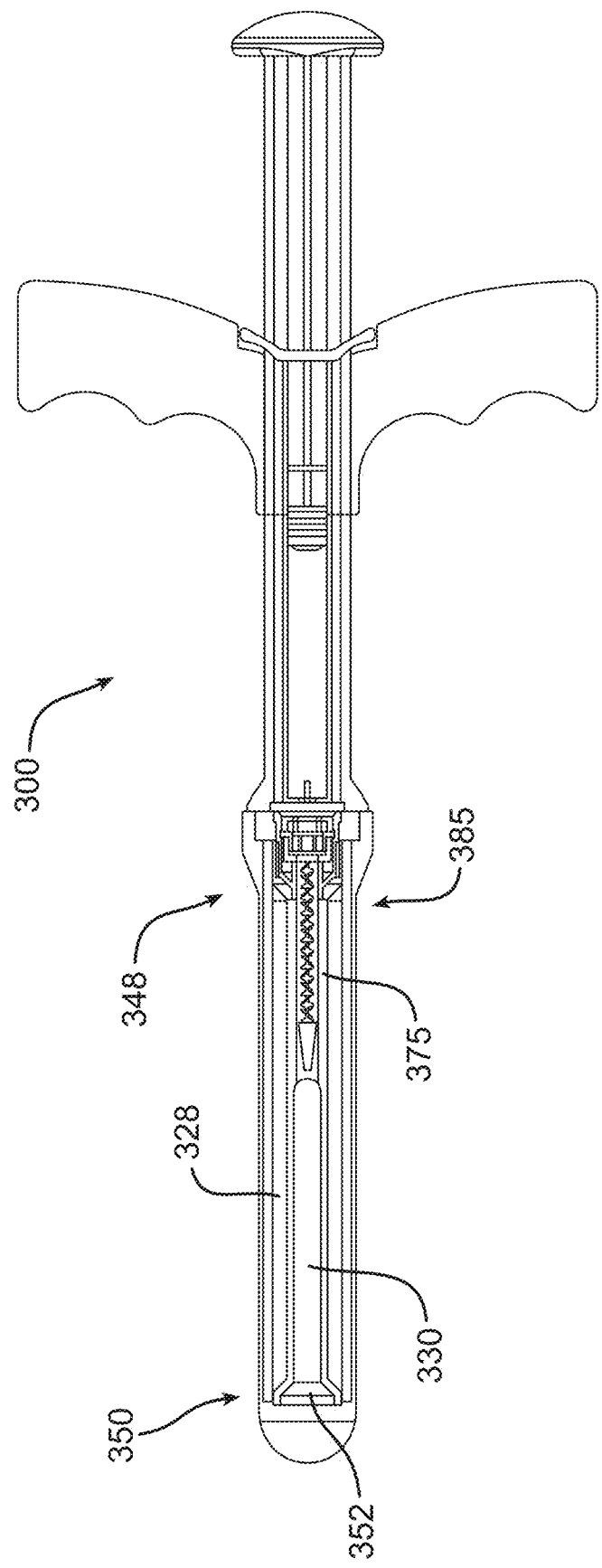
FIG. 23A is a cross-sectional top view of the sealant delivery device shown in FIGS. 21A-21B and 22.
Figure 23B:
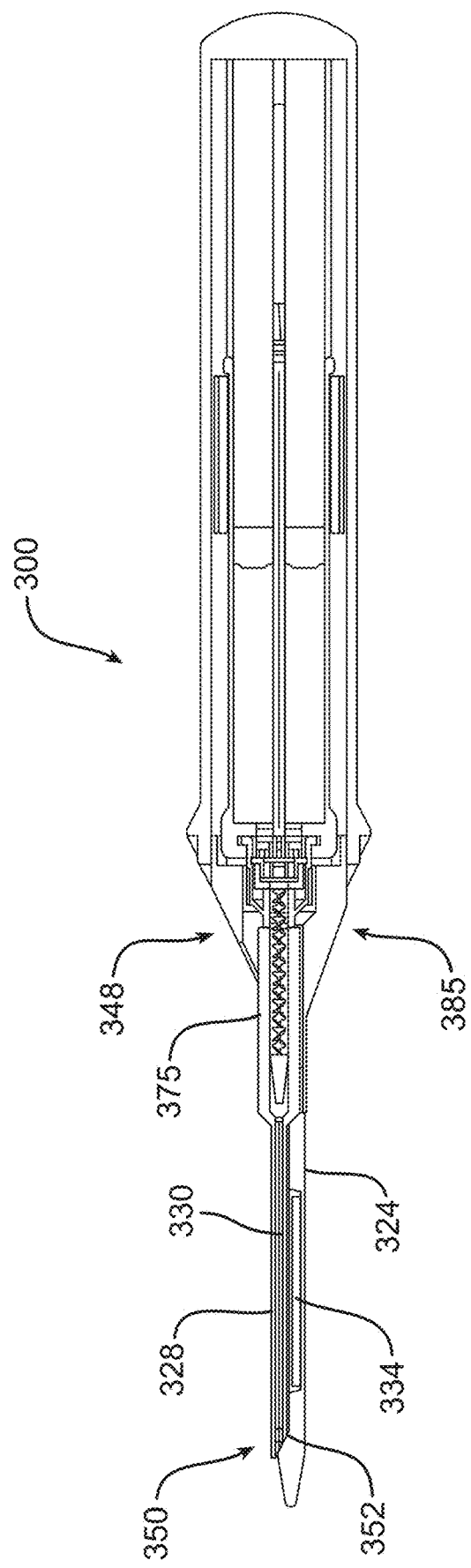
FIG. 23B is a cross-sectional side view of the sealant delivery device shown in FIGS. 21A-21B and 22.
Figure 23C:
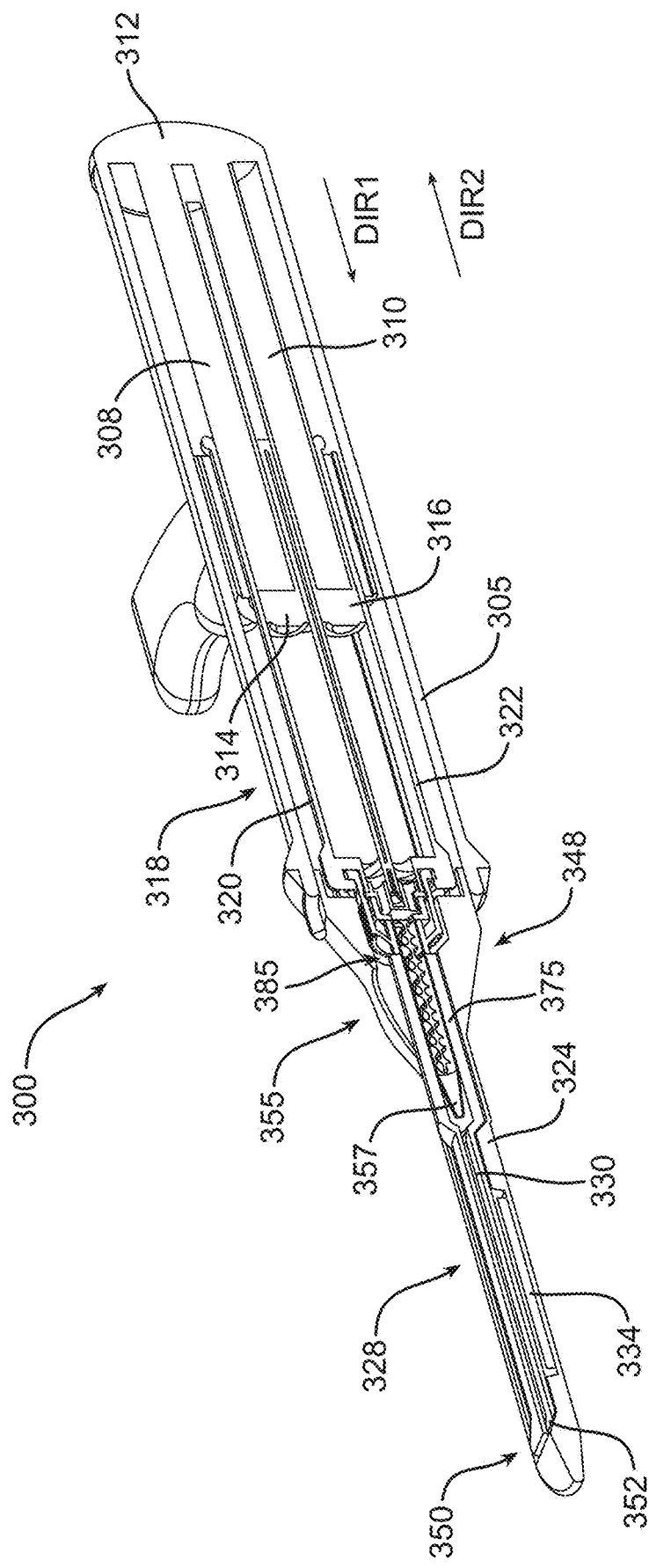
FIG. 23C is a cross-sectional perspective view of the sealant delivery device shown in FIGS. 21A-21B and 22.

Referring to FIGS. 23A-23C, in one embodiment, the protective cover 328 preferably has a proximal end 348 and a distal end 350. In one embodiment, the protective cover 328 preferably includes a sealant dispensing channel 330 that extends along the length of the protective cover 328 between the proximal end 348 and the distal end 350 thereof. In one embodiment, the protective cover 328 preferably includes a dispensing opening 352 located adjacent the distal end 350 of the protective cover 328. In one embodiment, a flowable sealant that is directed into an inlet opening 385 (FIG. 22) located at the proximal end 348 of the protective cover 328 is further directed into the sealant dispensing channel 330 and the sealant dispensing opening 352 at the distal end 350 of the protective cover 328 for being expressed onto the matrix 334 disposed within the tray 324 of the sealant delivery device 300 (FIG. 10).

Referring to FIG. 23C, in one embodiment, the sealant delivery device 300 preferably includes the housing 305 having the palm stop 312. The tray 324 is secured to the distal end of the housing 305. The housing 305 has the first plunger 308 and the second plunger 310. The first piston 314 is secured to the distal end of the first plunger 308 and the second piston 316 is secured to the distal end of the second plunger 310.

Figure 24:
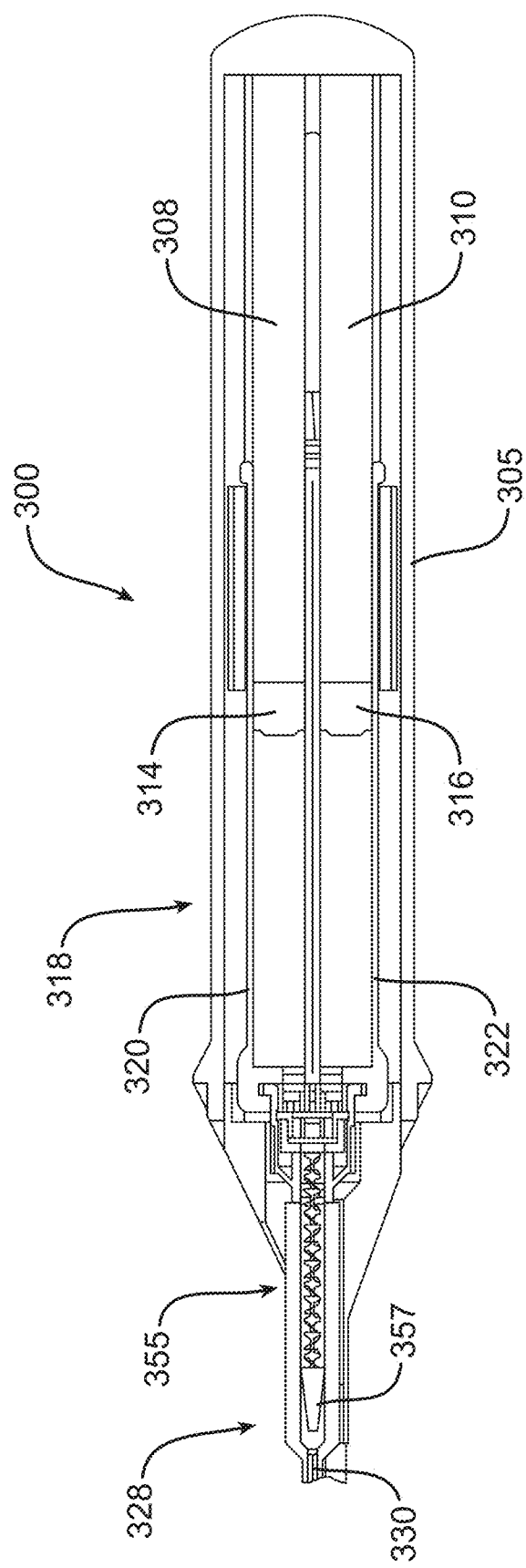
FIG. 24 is a magnified cross-sectional view of a proximal end of the sealant delivery device shown in FIGS. 21A-21B and 22.

Referring to FIGS. 23C and 24, in one embodiment, the sealant delivery device 300 preferably includes the dual barrel syringe 318 disposed within the housing 305. The dual barrel syringe 318 preferably includes the first syringe barrel 320 and the second syringe barrel 322. In one embodiment, the first plunger 308 and the first piston 314 are preferably disposed within the first syringe barrel 320. In one embodiment, the second plunger 310 and the second piston 316 are preferably disposed within the second syringe barrel 322. In one embodiment, dispensing openings located at the distal ends of the respective first and second syringe barrels 320, 322 are preferably in fluid communication with a proximal end of the mixing tip 355. The distal end of the sealant delivery tube 357 of the mixing tip 355 is preferably in fluid communication with the sealant dispensing channel 330 of the protective cover 328. In FIGS. 23C and 24, the protective cover 328 is preferably in an extended position relative to the tray 324 for covering and protecting the matrix 334 (FIG. 23C) disposed within the trough of the tray 324.

Figure 25:
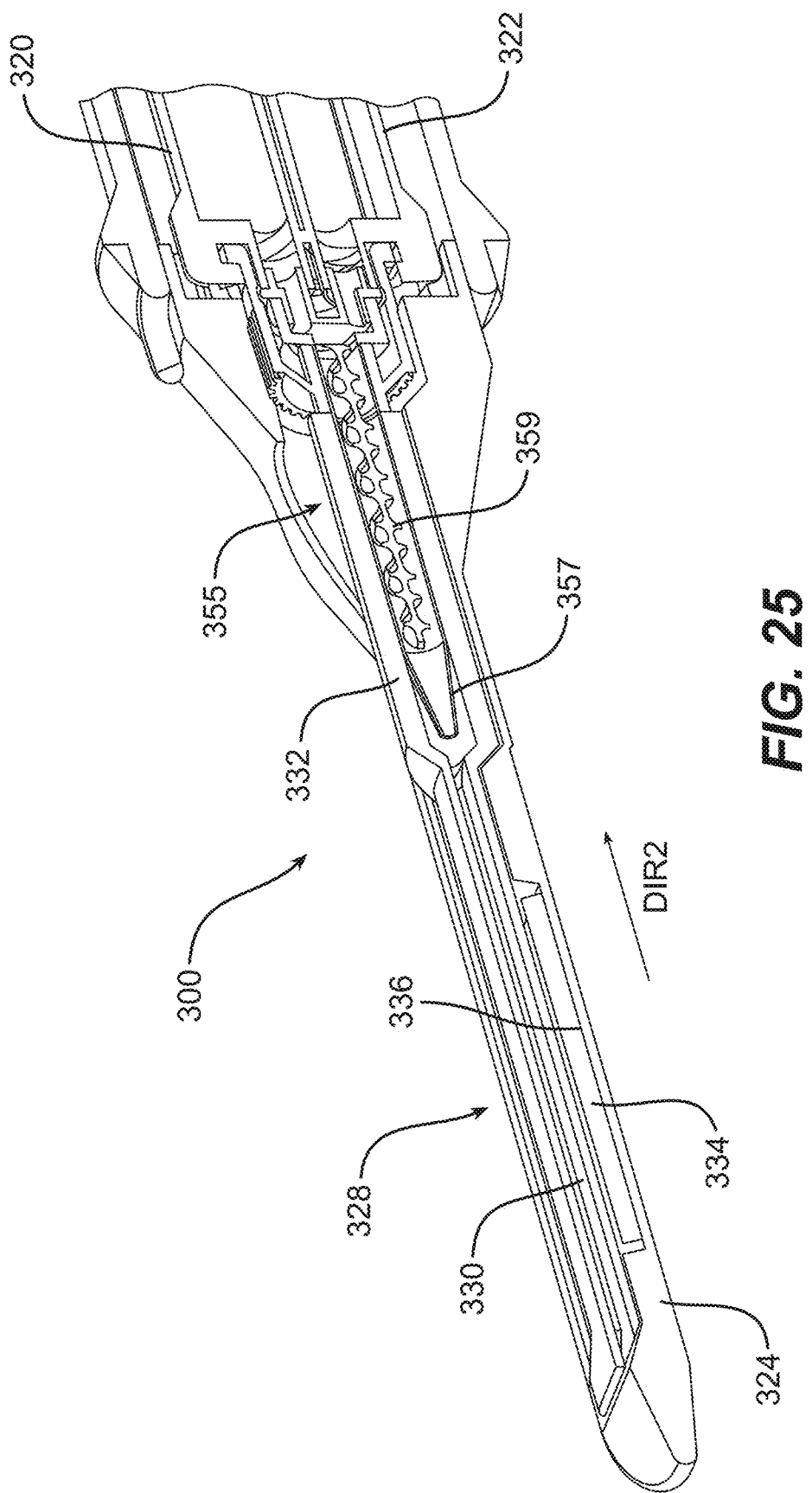
FIG. 25 is a perspective, cross-sectional view of a distal end of the sealant delivery device shown in FIGS. 21A-21B and 22.

Referring to FIGS. 25 and 26, in one embodiment, the matrix 334 is preferably disposed within the trough 336 of the tray 324. The protective cover 328 preferably overlies the matrix 334 and the tray 324 for protecting the matrix 334 within the tray. The distal end of the sealant delivery tube 357 of the mixing tip 355 is preferably in fluid communication with the mixing tip connector 332 at the proximal end of the protective cover 328. The flowable sealant mixture that passes through the static mixer 359 of the mixing tip 355 is preferably directed into the sealant dispensing channel 330 of the protective cover 328 for being dispensed onto the matrix 334 as the protective cover 328 is retracted in the proximal direction DIR2 relative to the tray 324 and the matrix 334.

In one embodiment, with the actuator 325 in an extended position relative to the palm stop 312 of the housing 305 (FIG. 23C), the protective cover 328 is in a fully extended position for covering the matrix 334 disposed within the trough 336 of the tray 324. Prior to the actuator 325 being pulled in the proximal direction DIR2, the first and second parts of the sealant remain within the respective first and second syringe barrels 320, 322 and are not yet mixed together nor directed into the mixing tip 355 of the sealant delivery device 300.

Referring to FIGS. 23C and 27, in one embodiment, as the actuator 325 (FIG. 230) is pulled in the proximal direction DIR2 toward the palm stop 312, the actuator 325 pulls the grip 335 (FIG. 21B) at the proximal end of the dual barrel syringe 218 in the proximal direction, whereupon the plungers force the first and second parts of the sealant to flow distally into the mixing tip 355 (FIG. 26), whereupon the two parts of the sealant are mixed together to form the sealant. Simultaneously, at the same time that the two parts of the sealant are mixed together, the protective cover 328, which is coupled with the actuator 325, is retracted in the proximal direction DIR2 for at least partially exposing the matrix 334 that is disposed within the trough 336 of the tray 324. As the protective cover 328 moves proximally in the direction DIR2 for uncovering the matrix 334, the sealant mixture preferably flows in the distal direction DIR1 and through the sealant dispensing channel 330 of the protective cover 328 for being dispensed from the sealant dispensing opening 352 onto the matrix 334.

In one embodiment, once the protective cover 328 has been moved proximally into a fully retracted position relative to the tray 324, the matrix 334 is exposed so that it may be applied over target tissue for stopping and/or controlling bleeding. As the protective cover 328 slides in the proximal direction DIR2, the flowable sealant moves through the sealant dispensing channel 330 in the distal direction DIR1 for being dispensed onto the matrix 334.

Figure 28A:
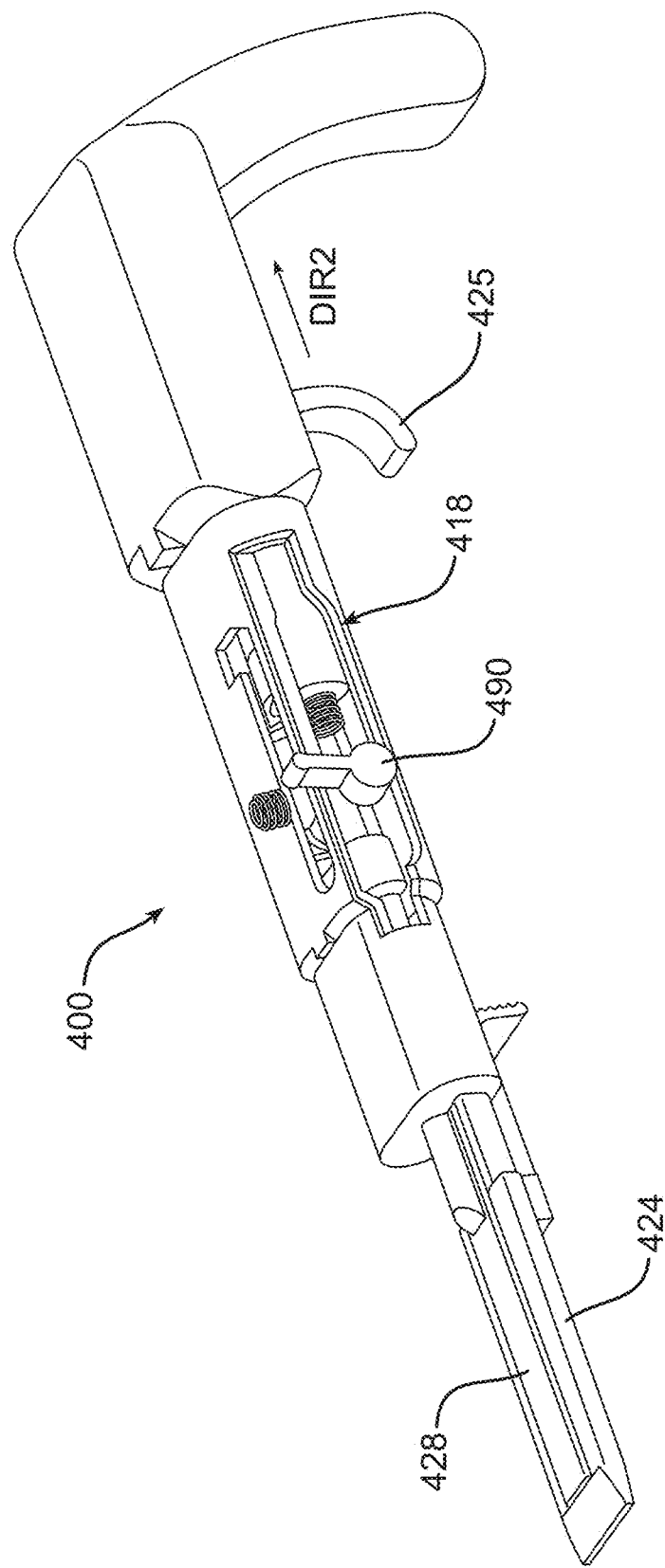
FIG. 28A is a perspective view of a sealant delivery device, in accordance with one embodiment of the present patent application.
Figure 28B:
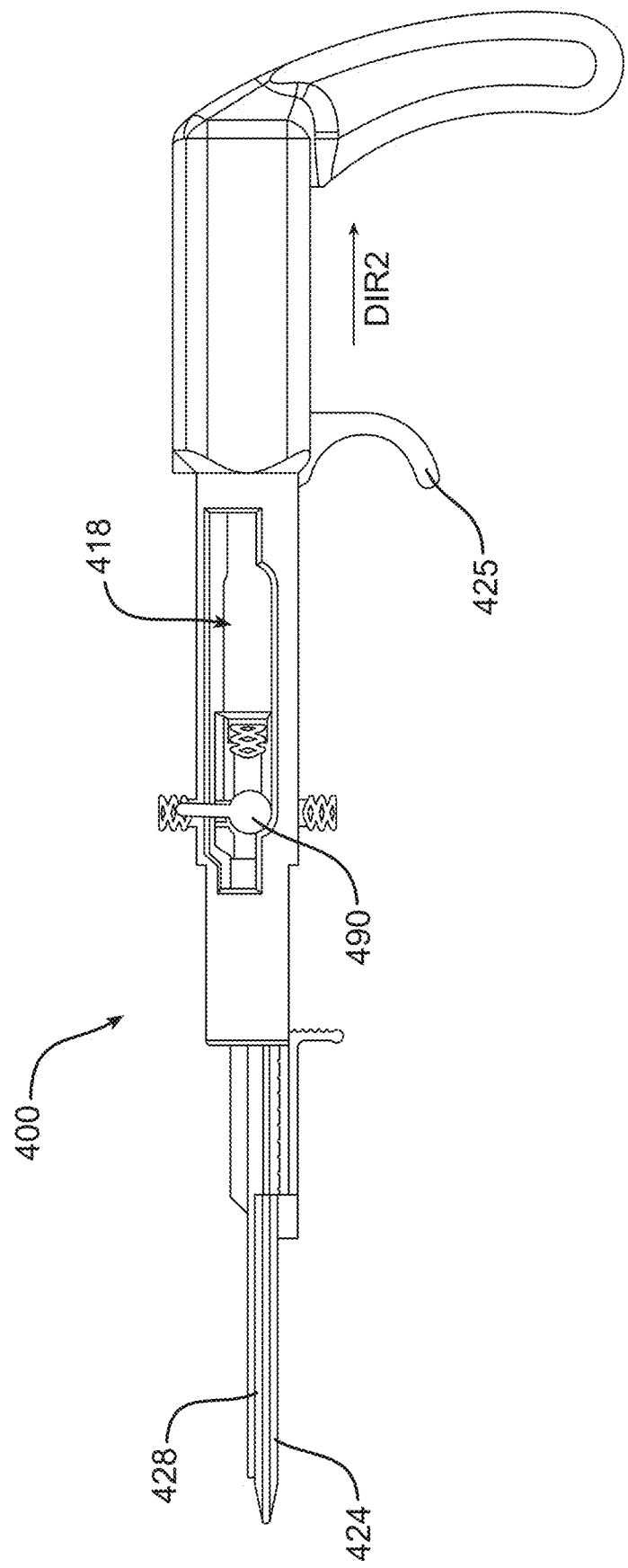
FIG. 28B is a side elevation view of the sealant delivery device shown in FIG. 28A.

Referring to FIGS. 28A and 28B, in one embodiment, a sealant delivery device 400 may have a structure and/or may operate in a manner that is similar to the sealant delivery device disclosed in FIGS. 9A-20B of the present patent application. In one embodiment, the sealant delivery device 400 preferably includes a three way luer 490 that enables the component parts of a flowable, curable sealant held within a dual barrel syringe 418 to be reconstituted prior to being expressed onto a matrix that is disposed within a tray 424. The sealant delivery device 400 preferably includes a trigger 425 that may be squeezed in a proximal direction DIR2 for retracting a protective cover 430 as the sealant is mixed and expressed onto the matrix disposed within the tray 424.

Figure 29A:
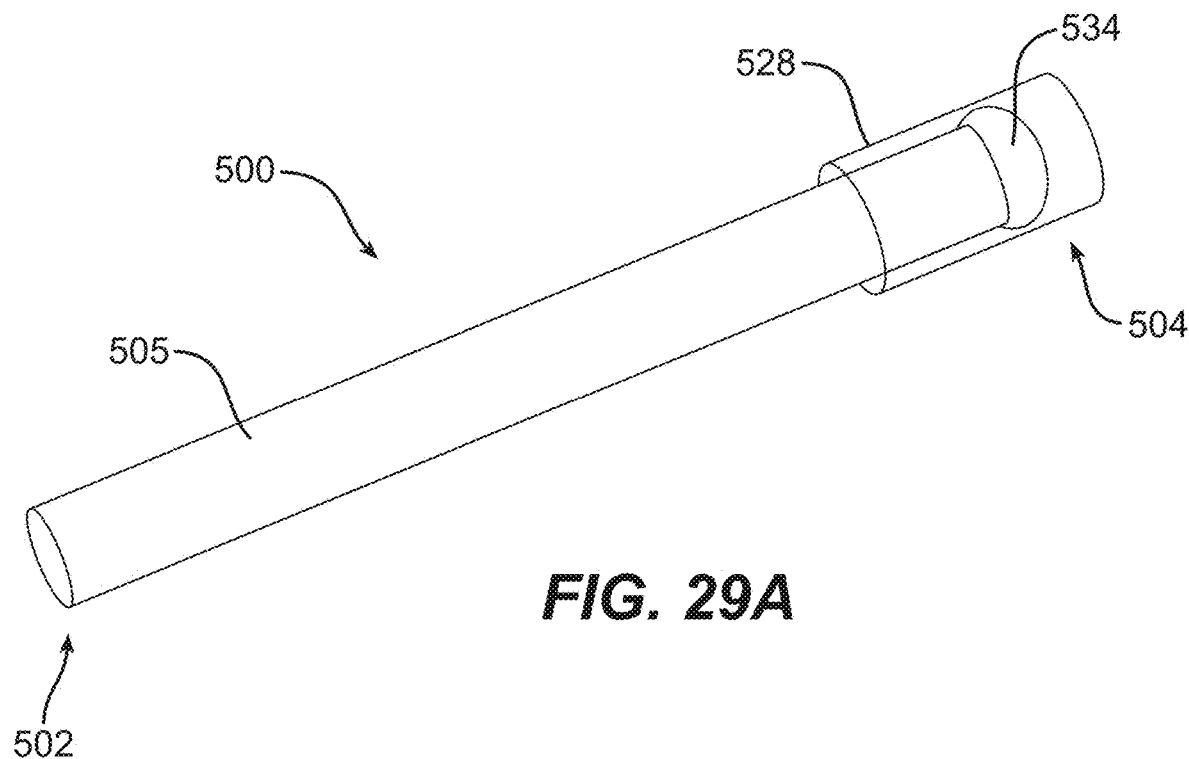
FIG. 29A is a side view of a sealant delivery device including a matrix and a protective cover for the matrix that is in an extended position, in accordance with one embodiment of the present patent application.
Figure 29B:
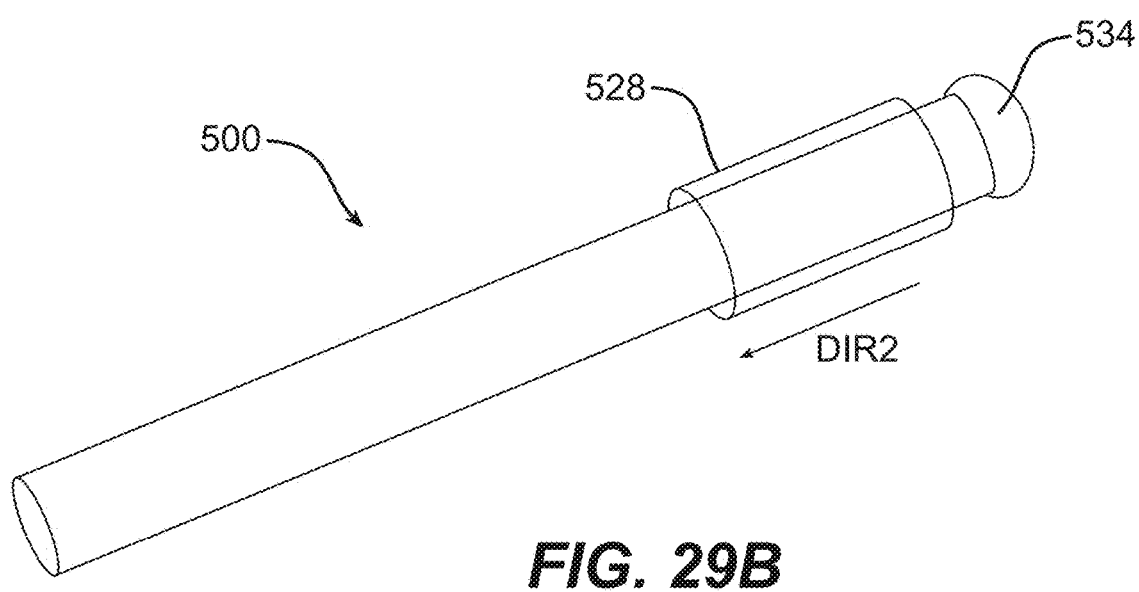
FIG. 29B is a perspective view of the sealant delivery device of FIG. 29A with the protective cover in a retracted position for exposing the matrix, in accordance with one embodiment of the present patent application.

Referring to FIGS. 29A and 29B, in one embodiment, a sealant delivery device 500 preferable includes a proximal end 502, a distal end 504, and a shaft 505 that extends along the length of the sealant delivery device from the proximal and 502 to the distal end 504. A matrix 505 (e.g., a medical textile; a hemostatic substrate) is releasably secured to the distal end 504 of the elongated shaft 505. A protective cover 528 is moveable between an extended position shown in FIG. 29A and a retracted position shown in FIG. 29B.

With the protective cover 528 in the extended position shown in FIG. 29A, the matrix 534 is protected from contacting surrounding tissue as the matrix is advanced to target tissue inside a patient. Once the matrix 534 has been positioned adjacent the target tissue, the protective cover 528 may be retracted into the position shown in FIG. 29B for exposing the matrix 534 so that the matrix may be secured over the target tissue for controlling and/or stopping bleeding of the target tissue.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:
1. A sealant delivery device comprising:
   a housing;
   a matrix container connected with a distal end of said housing and being moveable between closed and opened positions;
   a matrix disposed within said matrix container;
   a sealant dispensing system in fluid communication with said matrix container and being configured for dispensing a sealant onto said matrix disposed within said matrix container;
   an actuator coupled with said sealant dispensing system and said matrix container, wherein said actuator is engageable for moving said matrix container from the closed position to the opened position for exposing said matrix and for activating said sealant dispensing system to express said sealant onto said matrix.

2. The sealant delivery device as claimed in claim 1, wherein said sealant delivery device is configured for opening said matrix container while simultaneously expressing said sealant onto said matrix.

3. The sealant delivery device as claimed in claim 1, wherein said matrix container comprises:
   a tray having a proximal end connected with the distal end of said housing and a distal end that defines a distal-most end of said sealant delivery device;
   a protective cover that overlies said tray and that is coupled with said actuator, wherein said protective cover is moveable between an extended position that defines the closed position of said matrix container and a retracted position that defines the opened position of said matrix container.

4. The sealant delivery device as claimed in claim 3, wherein said protective cover is configured to move simultaneously with said actuator as said actuator is pulled toward the proximal end of said housing.

5. The sealant delivery device as claimed in claim 3, wherein said tray includes a trough that is configured to receive said matrix that is disposed within said matrix container.

6. The sealant delivery device as claimed in claim 3, wherein said protective cover comprises:
   a sealant dispensing channel that extends along the length of said protective cover and that is in fluid communication with said sealant dispensing system;
   a sealant dispensing opening located at a distal end of said sealant dispensing channel that is configured for expressing said sealant onto said matrix as said protective cover moves from the closed position to the opened position.

7. The sealant delivery device as claimed in claim 1, wherein said actuator comprises:
   a handle secured to a proximal end of said housing;
   a trigger coupled said housing and projecting from an underside of said housing, wherein said trigger is squeezable toward said handle and the proximal end of said housing for activating said sealant dispensing system while simultaneously retracting said protective cover toward the proximal end of said housing for moving said protective cover into the open position.

8. The sealant delivery device as claimed in claim 7, wherein said sealant dispensing system comprises:
   a dual barrel syringe disposed within said housing including a first syringe barrel containing a first part of said sealant and a second syringe barrel containing a second part of said sealant;
   a first syringe plunger disposed within said first syringe barrel and having a proximal end connected with the proximal end of said housing;

a second syringe plunger disposed within said second syringe barrel and having a proximal end connected with the proximal end of said housing.

9. The sealant delivery device as claimed in claim 8, wherein said trigger is coupled with said dual barrel syringe for pulling said dual barrel syringe toward the proximal end of said housing when said trigger is squeezed toward said handle and the proximal end of said housing.

10. The sealant delivery device as claimed in claim 9, wherein when said trigger is squeezed toward the proximal end of said housing, said first syringe plunger forces the first part of said sealant from the distal end of said first syringe barrel and said second syringe plunger forces the second part of said sealant from the distal end of said second syringe barrel.

11. The sealant delivery device as claimed in claim 10, further comprising a sealant mixer disposed between said first and second syringe barrels and said fluid dispensing channel of said protective cover for mixing the first and second parts of said sealant together and delivering said mixed sealant into said sealant dispensing channel of said protective cover.

12. The sealant delivery device as claimed in claim 11, wherein said sealant mixer comprises:
a sealant mixing tube having a proximal and a distal end;
a static mixer disposed within said sealant mixing tube;
a syringe barrel connector coupled with the proximal end of said sealant mixing tube for forming a fluid connection between distal ends of said respective first and second syringe barrels and said sealant mixing tube.

13. The sealant delivery device as claimed in claim 12, wherein said dual barrel syringe, said sealant mixer and said protective cover move together toward the proximal end of said housing as said trigger is squeezed toward the proximal end of said housing.

14. The sealant delivery device as claimed in claim 1, wherein said matrix is selected from the group consisting of hemostatic substrates, medical textiles, biocompatible matrices, and biocompatible substrates.

15. A sealant delivery device comprising:
a housing having a proximal end and a distal end;
a textile container connected with the distal end of said housing;
a textile disposed within said textile container;
said textile container including a protective cover that is movable between an extended position and a retracted position, said protective cover having a sealant dispensing channel extending along the length thereof;
a sealant dispensing system in fluid communication with said sealant dispensing channel of said protective cover;
an actuator coupled with said sealant dispensing system and said protective cover of said textile container, wherein said actuator is engageable for moving said protective cover into the retracted position for opening said textile container to expose said textile and for activating said sealant dispensing system to express said sealant onto said matrix.

16. The sealant delivery device as claimed in claim 15, wherein said sealant delivery device is configured so that said matrix container opens while said sealant is simultaneously expressed onto said matrix disposed within said matrix container.

17. The sealant delivery device as claimed in claim 15, wherein said protective cover comprises:
said sealant dispensing channel extending along the length of said protective cover and being in fluid communication with said sealant dispensing system;
a sealant dispensing opening located at a distal end of said sealant dispensing channel that is configured for expressing said sealant onto said matrix as said protective cover moves into the retracted position for opening said matrix container.

18. The sealant delivery device as claimed in claim 15, wherein said actuator comprises:
a handle secured to the proximal end of said housing;
a trigger coupled said housing and being slidable between the proximal and distal ends of said housing, wherein said trigger is squeezable toward said handle and the proximal end of said housing for activating said sealant dispensing system while simultaneously moving said protective cover into the retracted position for opening said matrix container.

19. The sealant delivery device as claimed in claim 18, wherein said sealant dispensing system comprises:
a dual barrel syringe disposed within said housing including a first syringe barrel containing a first part of said sealant and a second syringe barrel containing a second part of said sealant;
a first syringe plunger disposed within said first syringe barrel and having a proximal end connected with the proximal end of said housing;
a second syringe plunger disposed within said second syringe barrel and having a proximal end connected with the proximal end of said housing.

20. The sealant delivery device as claimed in claim 19, wherein said trigger is coupled with said dual barrel syringe for pulling said dual barrel syringe toward the proximal end of said housing when said trigger is squeezed toward said handle and the proximal end of said housing, wherein when said trigger is squeezed toward the proximal end of said housing, said first syringe plunger forces the first part of said sealant from the distal end of said first syringe barrel and said second syringe plunger forces the second part of said sealant from the distal end of said second syringe barrel, and wherein said dual barrel syringe and said protective cover move together toward the proximal end of said housing as said trigger is squeezed toward the proximal end of said housing.

21. The sealant delivery device as claimed in claim 20, further comprising:
a sealant mixer disposed between said first and second syringe barrels and said fluid dispensing channel of said protective cover for mixing said first and second parts of said sealant together and delivering said mixed sealant into said sealant dispensing channel of said protective cover;
wherein said sealant mixer comprises
a sealant mixing tube having a proximal and a distal end,
a static mixer disposed withing said sealant mixing tube, and
a syringe barrel connector coupled with the proximal end of said sealant mixing tube for providing fluid communication between distal ends of said respective first and second syringe barrels and said sealant mixing tube.

22. A method of controlling bleeding comprising:
obtaining a sealant delivery device including a housing, a matrix container, a matrix disposed within said matrix container, a sealant delivery system in fluid communication with said matrix container, and an actuator for opening said matrix container to expose said matrix and expressing a sealant from said sealant delivery system onto said matrix;
pulling said actuator toward a proximal end of said housing for opening said matrix container to expose said matrix and express said sealant onto said matrix;
using a component of said matrix container to press said matrix and said sealant expressed onto said matrix against target tissue for controlling bleeding of the target tissue.

23. The method as claimed in claim 22, further comprising simultaneously opening said matrix container and expressing said sealant onto said matrix.

* * * * *